(12) United States Patent
Boudry et al.

(10) Patent No.: US 12,125,662 B2
(45) Date of Patent: Oct. 22, 2024

(54) CORRECTION OF INTRA-SCAN FOCAL-SPOT DISPLACEMENT

(71) Applicant: GE Precision Healthcare LLC, Wauwatosa, WI (US)

(72) Inventors: John M Boudry, Waukesha, WI (US); Ryan J Lemminger, New Berlin, WI (US); Adam Israel Cohen, Milwaukee, WI (US); Jean-Francois Larroux, Hauts-de-Seine (FR)

(73) Assignee: GE Precision Healthcare LLC, Waukesha, WI (US)

( * ) Notice: Subject to any disclaimer, the term of this patent is extended or adjusted under 35 U.S.C. 154(b) by 302 days.

(21) Appl. No.: 17/657,692

(22) Filed: Apr. 1, 2022

(65) Prior Publication Data
US 2023/0317398 A1    Oct. 5, 2023

(51) Int. Cl.
*H01J 35/14*     (2006.01)
*A61B 6/03*      (2006.01)
*A61B 6/40*      (2024.01)
*G01N 23/046*    (2018.01)

(52) U.S. Cl.
CPC ............ *H01J 35/153* (2019.05); *A61B 6/032* (2013.01); *A61B 6/4028* (2013.01); *G01N 23/046* (2013.01); *H01J 35/147* (2019.05); *H01J 2235/086* (2013.01)

(58) Field of Classification Search
CPC .. H01J 35/153; H01J 35/147; H01J 2235/086; A61B 6/032; A61B 6/4028; A61B 6/4429; A61B 6/02; A61B 6/4021; A61B 6/58; A61B 6/5258; A61B 5/055; A61B 6/502; A61B 6/54; A61B 6/582; G01N 23/046; G01N 23/044
See application file for complete search history.

(56) References Cited

U.S. PATENT DOCUMENTS

| | | | |
|---|---|---|---|
| 6,968,039 | B2 | 11/2005 | Lemaitre et al. |
| 8,891,727 | B2 | 11/2014 | Kurochi et al. |
| 10,383,203 | B2 | 8/2019 | Meiler et al. |
| 11,141,128 | B2 | 10/2021 | Jacob et al. |
| 2005/0094762 | A1 | 5/2005 | Dunham |
| 2015/0103972 | A1 | 4/2015 | Bredno et al. |
| 2015/0117618 | A1 | 4/2015 | Li |

(Continued)

OTHER PUBLICATIONS

EP application 23162022.0 filed Mar. 15, 2023—extended Search Report issued Aug. 2, 2023; 6 pages.

(Continued)

*Primary Examiner* — Marcus H Taningco
*Assistant Examiner* — Meenakshi S Sahu
(74) *Attorney, Agent, or Firm* — Amin, Turocy & Watson, LLP

(57) ABSTRACT

Systems/techniques that facilitate correction of intra-scan focal-spot displacement are provided. In various embodiments, a system can access a first gantry angle of a medical scanner. In various aspects, the system can determine a first displacement of a focal-spot of the medical scanner based on the first gantry angle, by referencing a mapping that correlates gantry angles to focal-spot displacements. In various instances, the system can compensate, via one or more focal-spot position adjusters of the medical scanner, for the first displacement.

20 Claims, 12 Drawing Sheets

(56) References Cited

U.S. PATENT DOCUMENTS

| | | |
|---|---|---|
| 2019/0216413 A1 | 7/2019 | Jin |
| 2020/0222024 A1* | 7/2020 | Edic .................... G01N 23/046 |
| 2022/0296202 A1 | 9/2022 | Zhan et al. |

OTHER PUBLICATIONS

GE Patent Application CT x-ray tube alignment by electronic methods, IPCOM000199661D, (Docket 246034), (assignee: GE Healthcare), 2010, 8 pages.

Flay, N. et al. | "Investigation of the focal spot drift in industrial cone-beam X-ray computed tomography. Digital Industrial Radiology and Computed Tomography". Digital Industrial Radiology and Computed Tomography (DIR 2015) Jun. 22-25, 2015, Belgium, Ghent—www.ndt.net/app.DIR2015, 10 pages.

Notice of Allowance received for U.S. Appl. No. 17/657,411, dated Aug. 23, 2024, 25 pages.

\* cited by examiner

CORRECTION OF INTRA-SCAN FOCAL-SPOT DISPLACEMENT

TECHNICAL FIELD

The subject disclosure relates generally to focal-spots of medical imaging devices, and more specifically to correction of intra-scan focal-spot displacement.

BACKGROUND

Within an X-ray tube of a medical imaging device, an electron beam is accelerated from a cathode to an anode, so as to produce X-rays. The area over which the electron beam strikes the anode is referred to as the focal-spot. Image artefacts can occur when the focal-spot is at an undesirable and/or unintended location.

Systems and/or techniques that can address one or more of these technical problems can be desirable.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate correction of intra-scan focal-spot displacement are described.

According to one or more embodiments, a system is provided. The system can comprise a computer-readable memory that can store computer-executable components. The system can further comprise a processor that can be operably coupled to the computer-readable memory and that can execute the computer-executable components stored in the computer-readable memory. In various embodiments, the computer-executable components can comprise a receiver component. In various aspects, the receiver component can access a first gantry angle of a medical scanner. In various instances, the computer-executable components can further comprise a displacement component. In various cases, the displacement component can determine a first displacement of a focal-spot of the medical scanner based on the first gantry angle, by referencing a mapping that correlates gantry angles to focal-spot displacements. In various aspects, the computer-executable components can further comprise an execution component. In various instances, the execution component can compensate, via one or more focal-spot position adjusters of the medical scanner, for the first displacement.

According to one or more embodiments, the above-described system can be implemented as a computer-implemented method and/or a computer program product.

DETAILED DESCRIPTION

Figure 1:
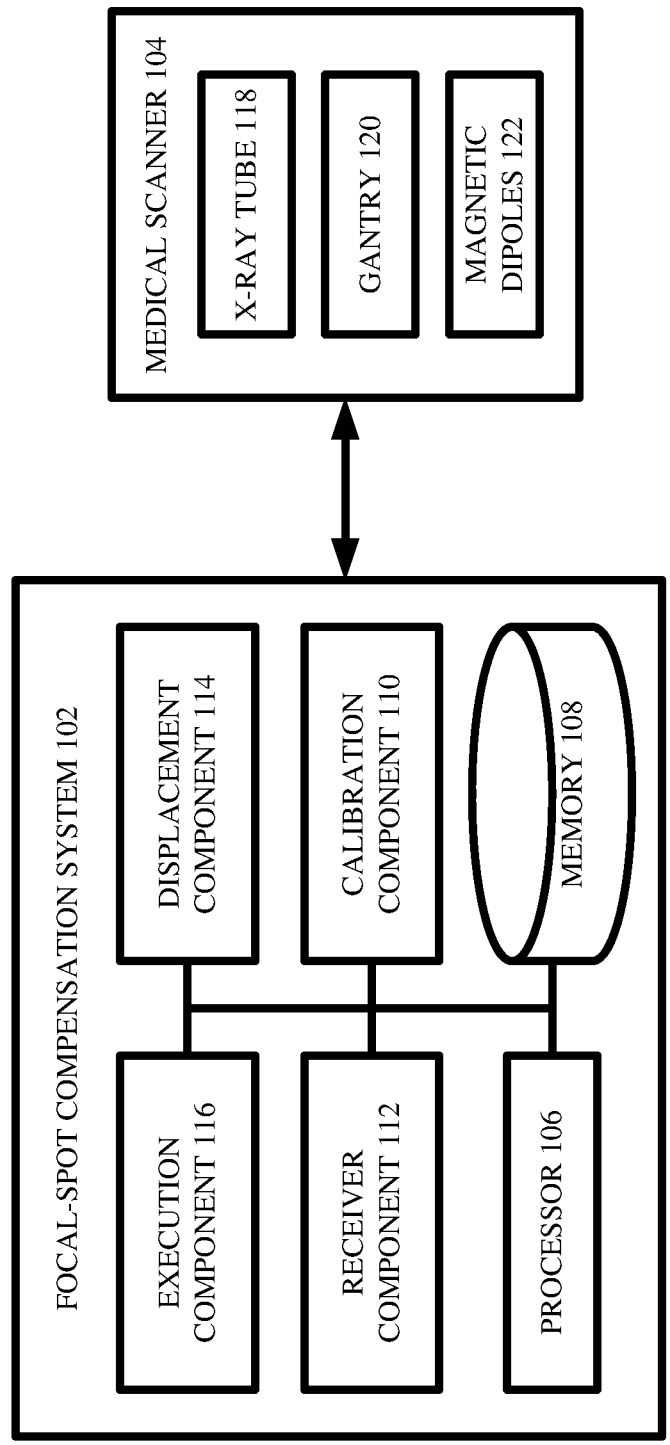
FIG. 1 illustrates a block diagram of an example, non-limiting system that facilitates correction of intra-scan focal-spot displacement in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Within an X-ray tube of a medical imaging device (e.g., a computed tomography (CT) scanner, a tomosynthesis mammography scanner), an electron beam can be accelerated from a cathode to an anode. As the electron beam strikes the anode, X-rays can be produced. The surface area over which the electron beam strikes can be referred to as the focal-spot (e.g., the focal-spot of the X-ray tube, and/or the focal-spot of the medical imaging device). Imaging artefacts can occur when the position of the focal-spot undesirably and/or unintentionally changes.

For example, the cathode and anode of an X-ray tube of a medical imaging device can be initially aligned (e.g., due to calibration processes). Over the course of many scan cycles, the cathode and anode can gradually become misaligned due to use and/or wear/tear. Such gradual misalignment can cause the focal-spot to gradually shift to a location that is different from its initial and/or desired location. As another example, the cathode and anode of the X-ray tube of the medical imaging device can be initially aligned (e.g., due to calibration processes), and the cathode and anode can become suddenly misaligned due to sudden external impacts experienced by the medical imaging device (e.g., which might occur when the medical imaging device is being packaged and/or transported from one room/place to another). Such sudden misalignment can cause the focal-spot to suddenly shift to a location that is different from its initial and/or desired location. In any case, when the focal-spot is at an undesired position, imaging artefacts (e.g., image streaks, image shadows) can be produced by the medical imaging device.

To address this issue of focal-spot movement, the X-ray tube can be outfitted and/or otherwise equipped with one or more electromagnets that can be leveraged to adjust the position of the focal-spot. More specifically, the electron beam that is transmitted from the cathode to the anode can bend due to interaction with a magnetic field, and such bending can cause the focal-spot to move from one location to another. Accordingly, if the focal-spot is currently at an undesired location, which undesired location might have been caused by gradual wear/tear and/or sudden external impacts, the one or more electromagnets can be actuated to create one or more magnetic fields (e.g., one or more magnetic dipoles) within the X-ray tube, and such one or more magnetic fields can cause the focal-spot to move from its current, undesired location to some predetermined, desired location. As those having ordinary skill in the art will appreciate, controllably adjusting the parameters (e.g., voltage and/or amperage) of the one or more electromagnets can correspondingly control how far and/or in what direction the focal-spot moves.

The inventors of various embodiments described herein recognized a significant technical problem that afflicts the above-described technique of focal-spot adjustment. Specifically, according to the above-described technique, when the focal-spot is at an undesired location, which might occur due to gradual wear/tear and/or sudden external impacts, the parameters of the one or more electromagnets can be adjusted so that the focal-spot moves to a desired location, and those particular parameters of the one or more electromagnets can be maintained (e.g., can be held constant) while the medical imaging device operates (e.g., during the performance/execution of one or more medical imaging scans) so as to help keep the focal-spot at the desired location.

However, although such technique might help to ensure that the focal-spot is at the desired location at the start of any given scan, the present inventors realized that such technique is not sufficient to ensure that the focal-spot remains at the desired location during and/or throughout the given scan. Indeed, this can be due to the fact that the X-ray tube can be implemented on a rotatable gantry of the medical imaging device. In particular, the present inventors recognized that the X-ray tube can be constantly exposed to the Earth's magnetic field, which can cause some amount of focal-spot deflection and/or displacement. Moreover, the present inventors further recognized that, as the X-ray tube rotates about the gantry during any given medical imaging scan, the orientation of the X-ray tube with respect to the Earth's magnetic field can constantly change. From the perspective of the X-ray tube, it can be considered as if the X-ray tube is stationary and the Earth's magnetic field is constantly changing direction/orientation during and/or throughout the given medical imaging scan. Thus, as the present inventors realized, the focal-spot can be considered as constantly moving and/or changing position from the perspective of the X-ray tube during/throughout the given medical imaging scan. Such constant changes in focal-spot position during a medical imaging scan can be referred to as intra-scan focal-spot displacement. Such intra-scan focal-spot displacement can cause the medical imaging device to produce significant imaging artefacts, which can be undesirable.

Accordingly, systems and/or techniques that can address one or more of these technical problems can be desirable.

Various embodiments described herein can address one or more of these technical problems. One or more embodiments described herein can include systems, computer-implemented methods, apparatus, and/or computer program products that can facilitate correction of intra-scan focal-spot displacement. That is, not only have the present inventors recognized the significant technical problem of intra-scan focal spot displacement, but the present inventors have also devised various systems and/or techniques for ameliorating intra-scan focal-spot displacement. In particular, the present inventors realized that the parameters (e.g., voltage and/or amperage) of the one or more electromagnets that are implemented with and/or inside the X-ray tube can be not constant during a medical imaging scan. Instead, the present inventors realized that such parameters can be changed and/or adjusted as a function of gantry angle of the X-ray tube. More specifically, at each gantry angle, the X-ray tube can be oriented with respect to the Earth's magnetic field in a unique and/or corresponding way, which can cause a unique and/or corresponding focal-spot displacement to occur in the X-ray tube. That is, for any given gantry angle, the X-ray tube can experience a unique focal-spot displacement that is caused by how the Earth's magnetic field interacts with the X-ray tube at the given gantry angle. Therefore, for any given gantry angle, the parameters of the one or more electromagnets can be adjusted so as to move the focal-spot by a magnitude and/or in a direction that counteracts, corrects, and/or otherwise compensates for such unique/corresponding focal-spot displacement.

In other words, the present inventors realized that intra-scan focal-spot-displacement can be caused by maintaining constant parameters of the one or more electromagnets of the X-ray tube for all gantry angles of the X-ray tube, and the present inventors further realized that intra-scan focal-spot displacement can be ameliorated by continually adjusting the parameters of the one or more electromagnets of the X-ray tube based on gantry angle of the X-ray tube (e.g., so that the electromagnets are set to different parameters for different gantry angles).

Furthermore, the present inventors realized that intra-scan focal-spot displacement can vary not just across gantry angles of the X-ray tube, but also across anode-cathode voltages of the X-ray tube. Thus, the present inventors further realized that intra-scan focal-spot displacement can be ameliorated by continually adjusting the parameters of the one or more electromagnets of the X-ray tube based on anode-cathode voltage of the X-ray tube (e.g., so that the electromagnets are set to different parameters for different anode-cathode voltages).

In various aspects, various embodiments described herein can be considered as a computerized tool (e.g., any suitable combination of computer-executable hardware and/or computer-executable software) that can facilitate correction of intra-scan focal-spot displacement. In various aspects, the computerized tool can comprise a calibration component, a receiver component, a displacement component, and/or an execution component.

In various embodiments, there can be a medical scanner that includes an X-ray tube and a gantry. In various aspects, the medical scanner can be any suitable type of medical imaging device as desired (e.g., a CT scanner, an MRI scanner). In any case, the X-ray tube of the medical scanner can rotate about the gantry (e.g., in some cases, the X-ray tube can rotate 360 degrees about the gantry; in other cases, the X-ray tube can rotate through any other suitable angular interval about the gantry).

In various instances, the X-ray tube can include one or more controllable magnetic dipoles that can be actuated to adjust the position of the focal-spot of the X-ray tube. As a non-limiting example, suppose that the surface area of the anode of the X-ray tube can be spanned by an x-axis and a y-axis. In other words, suppose that the position of the focal-spot on the anode can be described in terms of an x-coordinate and a y-coordinate. In such case, the X-ray tube can include a first electromagnet and a second electromagnet. In various instances, the first electromagnet can be oriented with respect to the X-ray tube in such a way so that, upon actuation, the first electromagnet can generate a first magnetic dipole (e.g., a first magnetic field) that can cause the focal-spot to move along the x-axis (e.g., in the positive x-direction or in the negative x-direction). As those having ordinary skill in the art will appreciate, the distance by which and/or direction in which the first magnetic dipole causes the focal-spot to move along the x-axis can depend upon the voltage and/or amperage that is fed to the first electromagnet (e.g., can depend upon the parameters of the first electromagnet). Similarly, in various cases, the second electromagnet can be oriented with respect to the X-ray tube in such a way (e.g., orthogonally to the first electromagnet) so that, upon actuation, the second electromagnet can generate a second magnetic dipole (e.g., a second magnetic field) that can cause the focal-spot to move along the y-axis (e.g., in the positive y-direction or in the negative y-direction). Again, as those having ordinary skill in the art will appreciate, the distance by which and/or direction in which the second magnetic dipole causes the focal-spot to move along the y-axis can depend upon the voltage and/or amperage that is fed to the second electromagnet (e.g., can depend upon the parameters of the second electromagnet). In any case, the one or more controllable magnetic dipoles can be implemented so as to controllably adjust the position of the focal-spot.

In various aspects, the X-ray tube can have at least two controllable and/or configurable settings. In various instances, a first controllable/configurable setting of the X-ray tube can be gantry angle (e.g., measured in degrees). In other words, the first controllable/configurable setting of the X-ray tube can be considered as the angular position of the X-ray tube about the gantry (e.g., the location about the gantry to which the X-ray tube is rotated). In various cases, a second controllable/configurable setting of the X-ray tube can be anode-cathode voltage. That is, the second controllable/configurable setting of the X-ray tube can be the electric voltage (e.g., measured in peak kilovolts) that is applied to the X-ray tube to accelerate the electron beam from the cathode to the anode. Those having ordinary skill in the art will appreciate that the anode-cathode voltage of the X-ray tube can be distinct and/or separate from the voltages that can be applied to generate the one or more controllable magnetic dipoles.

In any case, it can be desired to cause the medical scanner to perform/execute a medical imaging scan without experiencing intra-scan focal-spot displacement. The computerized tool described herein can facilitate such performance/execution.

In various embodiments, the calibration component of the computerized tool can electronically access and/or generate a voltage-angle-displacement mapping that is associated with the medical scanner. In various aspects, the voltage-angle-displacement mapping can correlate and/or otherwise link specific focal-spot displacements of the X-ray tube to specific gantry angles and/or to specific anode-cathode voltages of the X-ray tube. In other words, the voltage-angle-displacement mapping can be considered as indicating how the focal-spot of the X-ray tube becomes displaced by the Earth's magnetic field in response to particular gantry angles and/or particular anode-cathode voltages of the X-ray tube.

More specifically, there can be a set of possible anode-cathode voltages that can be assumed by the X-ray tube (e.g., such set can be considered as representing a total range and/or interval of anode-cathode voltages which the X-ray tube can be configured to sweep). Suppose that the set of possible anode-cathode voltages includes a voltages, for any suitable positive integer a. Moreover, there can be a set of possible gantry angles that can be assumed by the X-ray tube (e.g., such set can be considered as representing a total range and/or interval of gantry angles which the X-ray tube can be configured to sweep). Suppose that the set of possible gantry angles includes b angles, for any suitable positive integer b. Thus, the set of possible anode-cathode voltages and the set of possible gantry angles can be considered as collectively forming a total of ab unique voltage-angle pairs (e.g., voltage-angle tuples). In various aspects, the voltage-angle-displacement mapping can link and/or correlate each unique voltage-angle pair to a respectively corresponding focal-spot displacement, thereby yielding a total of ab focal-spot displacements. In various instances, a focal-spot displacement that corresponds to a given voltage-angle pair can be a two-element vector, where a first element of such two-element vector can indicate an x-displacement (e.g., measured in microns and/or millimeters, with direction along x-axis denoted by sign) of the focal-spot that is exhibited when the X-ray tube is configured according to the given voltage-angle pair, and where a second element of such two-element vector can indicate a y-displacement (e.g., measured in microns and/or millimeters, with direction along y-axis denoted by sign) of the focal-spot that is exhibited when the X-ray tube is configured according to the given voltage-angle pair. In various cases, such ab focal-spot displacements can be determined experimentally as follows: the medical scanner can be swept through all of the ab unique voltage-angle pairs, and, for each particular voltage-angle pair, the x-displacement and/or y-displacement that is exhibited by the focal-spot when the X-ray tube is configured according to such particular voltage-angle pair can be physically measured (e.g., via any suitable tungsten edge measuring technique).

In any case, the voltage-angle-displacement mapping can indicate how much and/or in what direction the focal-spot of the X-ray tube moves (e.g., due to interaction with the Earth's magnetic field) as a function of gantry angle of the X-ray tube and/or as a function of anode-cathode voltage of the X-ray tube.

In various embodiments, the receiver component of the computerized tool can electronically receive and/or otherwise electronically access a present gantry angle of the X-ray tube (e.g., a location about the gantry at which the X-ray tube is currently positioned and/or is about to be positioned) and/or a present anode-cathode voltage of the X-ray tube (e.g., an anode-cathode voltage to which the X-ray tube is currently set and/or is about to be set). In some instances, the receiver component can electronically retrieve the present gantry angle and/or the present anode-cathode voltage from any suitable centralized and/or decentralized data structure (e.g., graph data structure, relational data structure, hybrid data structure), whether remote from and/or local to the receiver component. In other instances, the receiver component can electronically retrieve the present gantry angle and/or the present anode-cathode voltage from the medical scanner itself. In still other cases, the receiver component can electronically measure, via any suitable position sensors and/or voltage sensors that are integrated with the medical scanner, the present gantry angle and/or the present anode-cathode voltage. In any case, the receiver component can electronically obtain and/or access the present gantry angle and/or the present anode-cathode voltage, such that other components of the computerized tool can electronically interact with (e.g., read, write, edit, manipulate) the present gantry angle and/or the present anode-cathode voltage.

In various embodiments, the displacement component of the computerized tool can electronically identify a present focal-spot displacement of the X-ray tube based on the present gantry angle and/or the present anode-cathode voltage, by referencing the voltage-angle-displacement mapping. In particular, and as mentioned above, the voltage-angle-displacement mapping can include a total of ab voltage-angle pairs, with each voltage-angle pair corresponding to a respective focal-spot displacement. Accordingly, in various instances, the displacement component can electronically search the voltage-angle-displacement mapping for a voltage-angle pair that matches the present gantry angle and/or the present anode-cathode voltage, and the focal-spot displacement that is listed in the voltage-angle-displacement mapping as corresponding to such voltage-angle pair can be considered as the present focal-spot displacement. Thus, in various aspects, the present focal-spot displacement can be considered as the amount of displacement (e.g., x-displacement from a desired x-position, and/or y-displacement from a desired y-position) that is and/or will be experienced by the focal-spot of the X-ray tube when the X-ray tube is set to the present gantry angle and/or the present anode-cathode voltage.

In various embodiments, the execution component of the computerized tool can electronically adjust and/or manipulate the one or more controllable magnetic dipoles, so as to correct, cancel, and/or otherwise compensate for the present focal-spot displacement. For example, as mentioned above, the X-ray tube can be outfitted and/or equipped with two electromagnets: a first electromagnet that is oriented so as to adjust the position of the focal-spot of the X-ray tube along the x-axis of the X-ray tube, and a second electromagnet that is oriented so as to adjust the position of the focal-spot of the X-ray tube along the y-axis of the X-ray tube. Moreover, in such case, the present focal-spot displacement can indicate both a present x-displacement (e.g., a distance between a current x-position of the focal-spot and a desired/predetermined x-position of the focal-spot) and a present y-displacement (e.g., a distance between a current y-position of the focal-spot and a desired/predetermined y-position of the focal-spot). Accordingly, as those having ordinary skill in the art will appreciate, electric current that is fed to the first electromagnet can be controlled so as to correct, cancel, and/or otherwise compensate for the present x-displacement of the focal-spot. For example, if the present x-displacement is 70 microns towards the positive side of the x-axis (e.g., if the focal-spot is currently 70 microns to the right of the desired x-position), then a certain amount and/or phase of electric current can be fed to the first electromagnet so as to cause the focal-spot to move 70 microns towards the negative side of the x-axis (e.g., so as to cause the focal-spot to move 70 microns leftward, so as to now be at the desired x-position). Likewise, as those having ordinary skill in the art will further appreciate, electric current that is fed to the second electromagnet can be controlled so as to correct, cancel, and/or otherwise compensate for the present y-displacement of the focal-spot. For instance, if the y-displacement is 23 microns towards the negative side of the y-axis (e.g., if the focal-spot is currently 23 microns below the desired y-position), then a certain amount and/or phase of electric current can be fed to the second electromagnet so as to cause the focal-spot to move toward the positive side of the y-axis by 23 microns (e.g., so as to cause the focal-spot to move 23 microns upward, so as to now be at the desired y-position). In any case, those having ordinary skill in the art will appreciate how the controllable magnetic dipoles (e.g., how electromagnets) can be controllably altered/adjusted so as to controllably adjust the position of the focal-spot.

In various aspects, the receiver component, the displacement component, and/or the execution component can repeat various of the above-described functionalities as many times as desired (e.g., can repeat the above-described functionalities for each gantry angle and/or for each anode-cathode voltage that is taken on by the X-ray tube). For example, the receiver component can electronically access a new gantry angle and/or a new anode-cathode voltage of the X-ray tube of the medical scanner, the displacement component can electronically identify a new focal-spot displacement based on the new gantry angle and/or the new anode-cathode voltage by referencing the voltage-angle-displacement mapping, and the execution component can electronically actuate/adjust the controllable magnetic dipoles so as to correct, cancel, and/or compensate for the new focal-spot displacement. In this way, the medical scanner can perform/execute a scan without experiencing intra-scan focal-spot displacement (e.g., because the scan can involve sequentially/chronologically sweeping the X-ray tube through multiple gantry angles and/or multiple anode-cathode voltages, the voltage-angle-displacement mapping can be continually referenced throughout the scan and the controllable magnetic dipoles can be continually adjusted throughout the scan so as to eliminate/reduce focal-spot displacements that would otherwise occur during the scan).

Various embodiments of the subject innovation can be employed to use hardware and/or software to solve problems that are highly technical in nature (e.g., to facilitate correction of intra-scan focal-spot displacement), that are not abstract and that cannot be performed as a set of mental acts by a human. Further, some of the processes performed can be performed by a specialized computer (e.g., CT scanner, MRI scanner, magnetic dipoles generated by electromagnets) for carrying out defined tasks related to correction of intra-scan focal-spot displacement. For example, such defined tasks can include: accessing, by a device operatively coupled to a processor, a first gantry angle of a medical scanner; determining, by the device, a first displacement of a focal-spot of the medical scanner based on the first gantry angle, by referencing a mapping that correlates gantry angles to focal-spot displacements; and compensating, by the device and via one or more magnetic dipoles of the medical scanner, for the first displacement. Such defined tasks can further include: accessing, by the device, a first voltage level of the medical scanner, wherein the mapping further correlates voltage levels to focal-spot displacements; and determining, by the device, the first displacement of the focal-spot of the medical scanner based on the first voltage level.

Such defined tasks are not performed manually by humans. Indeed, neither the human mind nor a human with pen and paper can electronically receive a gantry angle and/or an anode-cathode voltage of an X-ray tube of a medical scanner (e.g., a CT scanner, an MRI scanner), can electronically determine, via a voltage-angle-displacement mapping, a displacement of the focal-spot of the X-ray tube of the medical scanner based on the gantry angle and/or the anode-cathode voltage, and/or can electronically adjust one or more magnetic dipoles of the X-ray tube of the medical scanner so as to cancel, correct, and/or compensate for the displacement of the focal-spot (e.g., so as to cause the focal-spot to move in a direction opposite to that of the identified displacement and with a magnitude equal to that of the identified displacement). Instead, various embodiments described herein are inherently and inextricably tied to computer technology and cannot be implemented outside of a computing environment (e.g., a medical imaging scanner is an inherently-computerized device that can generate medical images by passing X-ray radiation through an object of interest, such as an anatomical structure of a patient; a computerized tool that can adjust operation of the medical imaging scanner so as to reduce/eliminate focal-spot displacement during and/or throughout a scan is likewise inherently-computerized and cannot be implemented in any sensible, practical, or reasonable way without computers).

Moreover, various embodiments can integrate into a practical application various teachings described herein relating to correction of intra-scan focal-spot displacement. As explained above, an X-ray tube of a medical scanner can be outfitted with one or more controllable magnetic dipoles for adjusting focal-spot position. Indeed, if the focal-spot is at an undesired location (e.g., due to gradual drift from wear/tear and/or due to sudden drift from external impact), then the one or more controllable magnetic dipoles can be set to particular parameters (e.g., particular amperage levels) so as to shift and/or translate the focal-spot back to a desired location, and the one or more controllable magnetic dipoles can be constantly and/or uniformly maintained at such parameters during/throughout a medical scan. Unfortunately, and as the present inventors recognized, although maintaining constant/uniform parameters for the controllable magnetic dipoles can cause the focal-spot to be at the desired location at the start/beginning of the medical scan, maintaining such constant/uniform parameters during/throughout the medical scan can cause the focal-spot to unintentionally and continually change position during/throughout the medical scan. Such unintentional and counterintuitive motion of the focal-spot during/throughout the medical scan can be referred to as intra-scan focal-spot displacement. More specifically, during the medical scan, the X-ray tube can sweep through different gantry angles and/or different anode-cathode voltages. At each unique gantry angle and/or at each unique anode-cathode voltage, the Earth's magnetic field can interact uniquely with the electron beam of the X-ray tube, which can yield a unique focal-spot displacement with respect to the X-ray tube. In other words, as the gantry angle and/or anode-cathode voltage changes during/throughout the medical scan, so too does the position of the focal-spot when the one or more controllable magnetic dipoles are held at constant/uniform parameters.

Fortunately, the present inventors realized that such intra-scan focal-spot displacement can be remedied and/or ameliorated by continually adjusting the parameters of the one or more controllable magnetic dipoles as a function of gantry angle and/or anode-cathode voltage. In other words, the present inventors recognized that intra-scan focal-spot displacement can be reduced by setting the one or more controllable magnetic dipoles to different parameters (e.g., different amperages) when the X-ray tube is at different gantry angles and/or different anode-cathode voltages. In still other words, the present inventors realized that a unique focal-spot displacement can occur (e.g., due to interaction with Earth's magnetic field) when the X-ray tube is positioned at a unique gantry angle and/or at a unique anode-cathode voltage, and such unique focal-spot displacement can be corrected and/or cancelled by appropriately adjusting the parameters of the one or more controllable magnetic dipoles. Accordingly, during a medical scan in which the X-ray tube sweeps through various gantry angles and/or anode-cathode voltages, the parameters of the one or more controllable magnetic dipoles can be continually adjusted, as opposed to being held constant/uniform, so as to eliminate/reduce intra-scan focal-spot displacement. A computerized tool that can reduce/ameliorate intra-scan focal-spot displacement in this way certainly constitutes a concrete and tangible technical improvement in the field of focal-spots of medical imaging scanners, and thus surely qualifies as a useful and practical application of computers.

Furthermore, various embodiments described herein can control real-world tangible devices based on the disclosed teachings. For example, various embodiments described herein can electronically control (e.g., power up, power down, calibrate) real-world magnetic dipoles (e.g., real-world electromagnets) that are integrated with real-world medical imaging scanners (e.g., CT scanners, MRI scanners).

It should be appreciated that the herein figures and description provide non-limiting examples and are not necessarily drawn to scale.

FIG. 1 illustrates a block diagram of an example, non-limiting system 100 that can facilitate correction of intra-scan focal-spot displacement in accordance with one or more embodiments described herein. As shown, a focal-spot compensation system 102 can be electronically integrated, via any suitable wired and/or wireless electronic connections, with a medical scanner 104.

In various embodiments, the medical scanner 104 can be any suitable medical imaging device as desired. For example, the medical scanner 104 can, in various aspects, be a CT scanner. As another example, the medical scanner 104 can, in various instances, be an MRI scanner. In any case, the medical scanner 104 can include an X-ray tube 118, a gantry 120, and/or one or more magnetic dipoles 122. In various aspects, the X-ray tube 118 can rotate to different angular positions about and/or along the gantry 120. Moreover, in various instances, the X-ray tube 118 can include a cathode (not shown) and an anode (not shown), where a voltage applied to such cathode and anode can cause an electron beam to be accelerated from the cathode to the anode. When the electron beam strikes the anode, X-ray radiation can be produced and can radiate and/or propagate toward a central bore of the gantry 120. When an object (e.g., an anatomical structure of a medical patient) is placed within the central bore of the gantry 120, the X-ray radiation can pass through the object and can be recorded by one or more row detectors (not shown) of the medical scanner 104, thereby yielding medical images (e.g., CT images, MRI images). This is shown with respect to FIG. 2.

Figure 2:
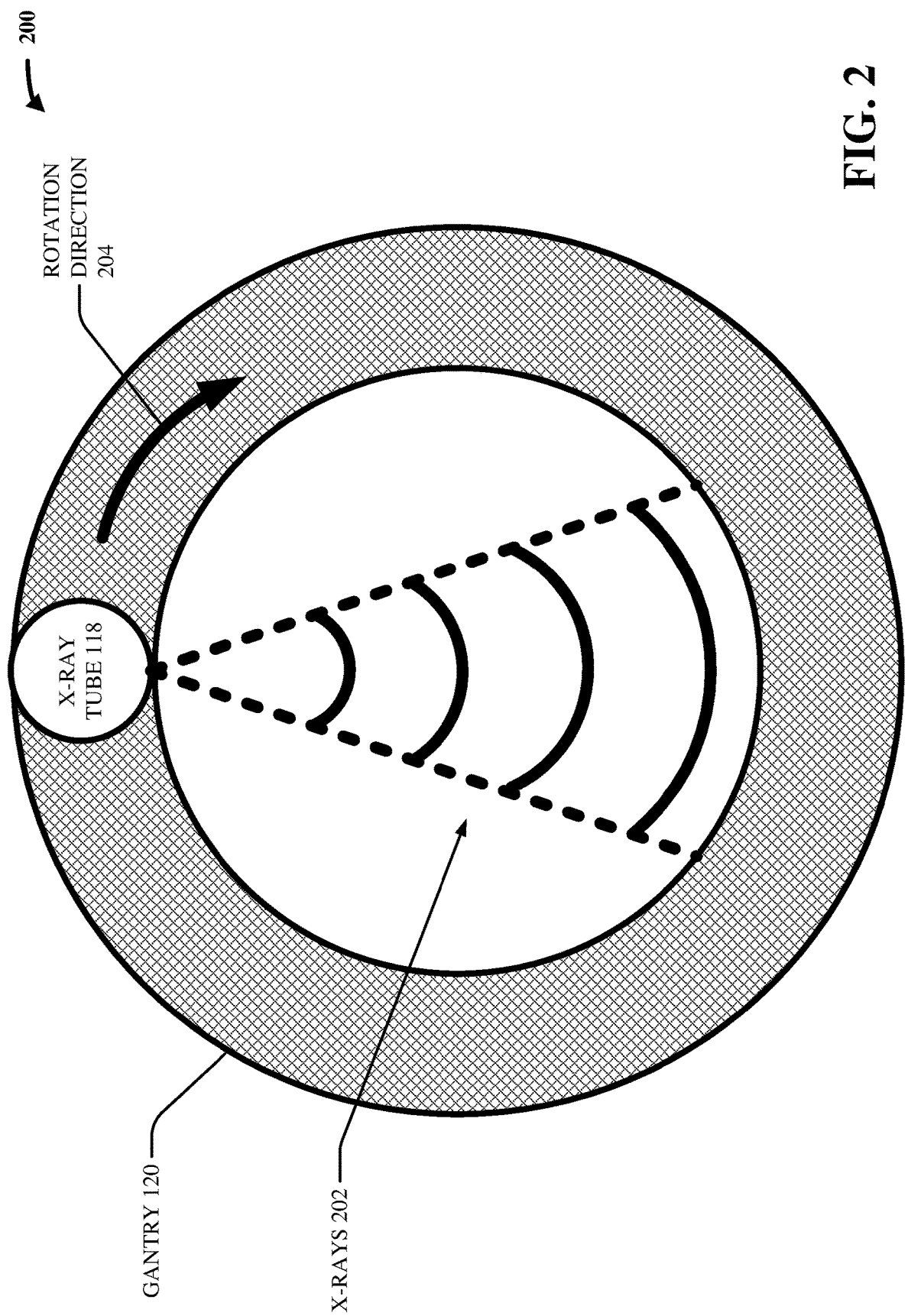
FIG. 2 illustrates an example, non-limiting block diagram of a medical scanner in accordance with one or more embodiments described herein.

FIG. 2 illustrates an example, non-limiting block diagram 200 of a medical scanner in accordance with one or more embodiments described herein. In other words, FIG. 2 shows a non-limiting example embodiment of the medical scanner 104. As shown, the gantry 120 can be a circular path and/or ring about which and/or along which the X-ray tube 118 can controllably rotate. As a non-limiting example, the X-ray tube 118 can emit one or more X-rays 202 radially toward a central bore of the gantry 120, and the X-ray tube 118 can change the direction of emission of the X-rays 202 by moving about/along the gantry 120 in a rotation direction 204. As those having ordinary skill in the art will appreciate, the location and/or position of the X-ray tube 118 along the gantry 120 can be described by a gantry angle (e.g., measured in degrees and/or radians), where the sign of the gantry angle can indicate a direction (e.g., counterclockwise and/or clockwise) in which the X-ray tube 118 has rotated about/along the gantry 120 from a reference position, and/or where the magnitude of the gantry angle can indicate how far the X-ray tube 118 has rotated about/along the gantry 120 from the reference position.

In various embodiments, the one or more magnetic dipoles 122 can be integrated on, with, within, and/or otherwise near the X-ray tube 118, so as to be able to adjust a focal-spot of the X-ray tube 118. In various aspects, the focal-spot of the X-ray tube 118 can be considered as the portion of the anode surface area which the electron beam strikes and/or impacts (e.g., portions of the anode surface area that are not struck and/or impacted by the electron beam can be considered as outside of the focal-spot). As mentioned above, the electron beam can bend due to interference with an external magnetic field. Accordingly, when the electron beam of the X-ray tube 118 is exposed to the one or more magnetic dipoles 122, the electron beam can bend, and the focal-spot can thus move and/or otherwise change its position. Thus, as those having ordinary skill in the art will appreciate, controllably altering the one or more magnetic dipoles 122 (e.g., controllably altering the strengths and/or orientations of the one or more magnetic dipoles 122) can cause the focal-spot of the X-ray tube 118 to controllably change its position. In various cases, the one or more magnetic dipoles 122 can be created and/or generated by any suitable electromagnets as desired (e.g., in such case, the strengths and/or orientations of the one or more magnetic dipoles 122 can be controllably adjusted by controlling how much and/or what phase of electric current is fed to such electromagnets). In various other cases, the one or more magnetic dipoles 122 can be created and/or generated by any suitable electrostatic techniques as desired.

Although the herein disclosure mainly describes various embodiments as implementing the one or more magnetic dipoles 122 to adjust the focal-spot of the X-ray tube 118, this is a mere non-limiting example for ease of explanation. Those having ordinary skill in the art will appreciate that any other suitable focal-spot position adjusters can be implemented as desired, such as electrostatic deflection electrodes.

In any case, the anode surface area of the X-ray tube 118 can be considered as being spanned by a reference frame. As a non-limiting example, such reference frame can include an x-axis and/or a y-axis that are orthogonal to each other. In such case, the position of the focal-spot of the X-ray tube 118 can be described by an x-coordinate and/or a y-coordinate. However, this use of Cartesian coordinates is a mere non-limiting example for purposes of explanation. Those having ordinary skill in the art will appreciate that the reference frame can be defined by any other suitable type of coordinates as desired (e.g., polar coordinates). In various aspects, the orientation of such reference frame (e.g., the orientation of the X-ray tube 118) can change as a function of gantry angle (e.g., can change with the position of the X-ray tube 118 about/along the gantry 120). This is shown with respect to FIG. 3.

Figure 3:
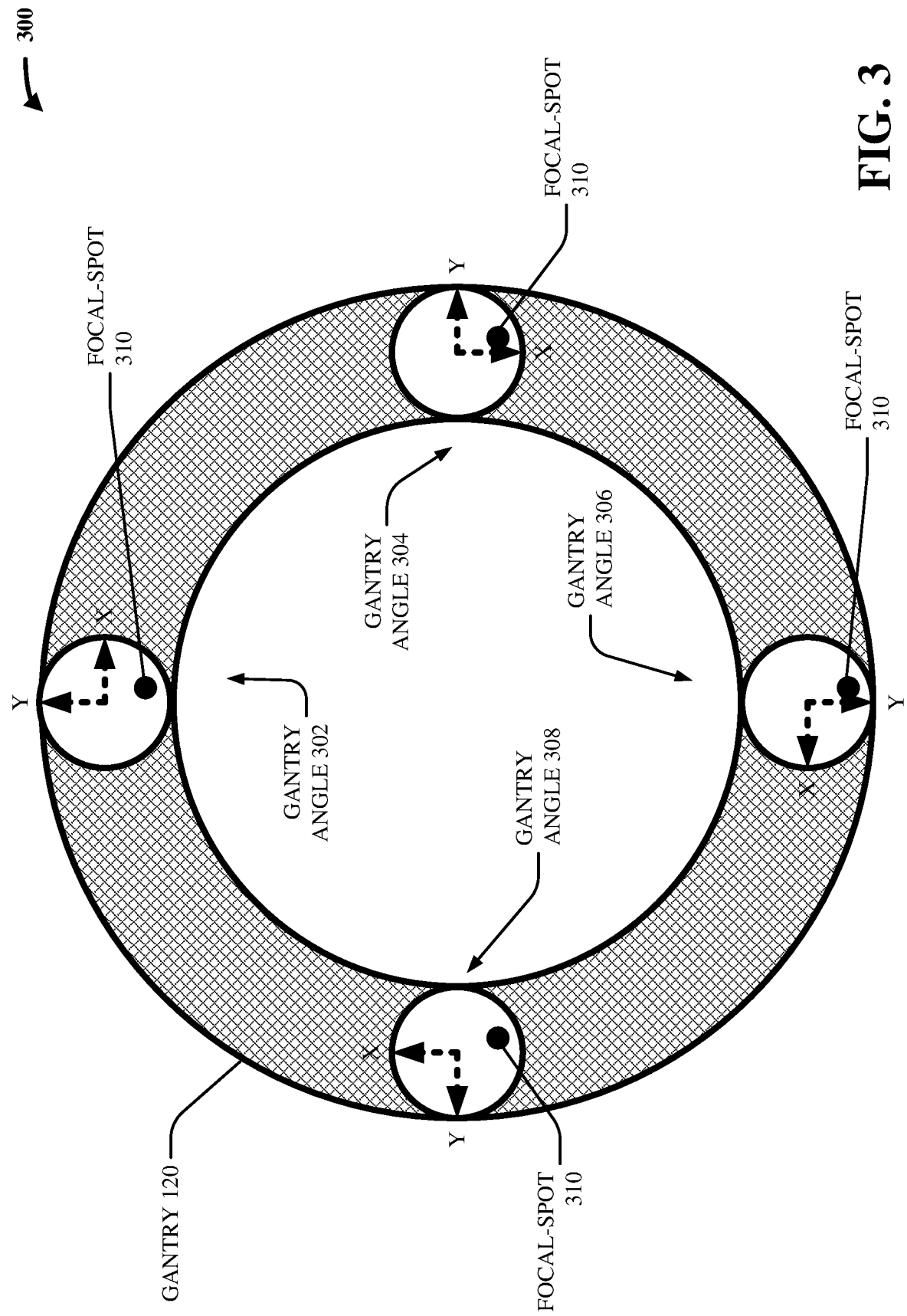
FIG. 3 illustrates an example, non-limiting block diagram showing how a focal-spot of an X-ray tube of a medical scanner can move with respect to the X-ray tube when the X-ray tube rotates about a gantry in accordance with one or more embodiments described herein.

FIG. 3 illustrates an example, non-limiting block diagram 300 showing how the focal-spot of the X-ray tube 118 can move with respect to the reference frame of the X-ray tube 118 as the X-ray tube 118 rotates about the gantry 120, in accordance with one or more embodiments described herein.

As mentioned above, the reference frame of the X-ray tube 118 can, in some cases, be defined by an x-axis and/or a y-axis that are orthogonal to each other. As can be seen, FIG. 3 depicts the orientation of such x-axis and/or y-axis of the X-ray tube 118 at four different gantry angles (e.g., at four different positions about/along the gantry 120): a gantry angle 302, a gantry angle 304, a gantry angle 306, and/or a gantry angle 308. As shown, the x-axis can point rightward and the y-axis can point upward when the X-ray tube 118 is positioned along the gantry 120 according to the gantry angle 302. As also shown, the x-axis can point downward and the y-axis can point rightward when the X-ray tube 118 is positioned along the gantry 120 according to the gantry angle 304 (e.g., the gantry angle 304 can be 90 degrees clockwise of the gantry angle 302). Moreover, the x-axis can point leftward and the y-axis can point downward when the X-ray tube 118 is positioned along the gantry 120 according to the gantry angle 306 (e.g., the gantry angle 306 can be 180 degrees clockwise of the gantry angle 302). Furthermore, the x-axis can point upward and the y-axis can point leftward when the X-ray tube 118 is positioned along the gantry 120 according to the gantry angle 308 (e.g., the gantry angle 308 can be 270 degrees clockwise of the gantry angle 302). Those having ordinary skill in the art will appreciate that these are mere non-limiting examples of gantry angles at which the X-ray tube 118 can be positioned about and/or along the gantry 120. In any case, the orientation of the X-ray tube 118 (e.g., the orientation of the x-axis and the y-axis) can change as the X-ray tube 118 rotates about/along the gantry 120.

In various aspects, although the reference frame and/or orientation of the X-ray tube 118 can change as the X-ray tube 118 rotates about/along the gantry 120, the orientation of the Earth's magnetic field (not shown) can remain stationary and/or can refrain from changing as the X-ray tube 118 rotates about/along the gantry 120. From the perspective of the X-ray tube 118, such relative motion can be inverted. That is, from the perspective of the X-ray tube 118, it can instead be considered as if the orientation and/or reference frame of the X-ray tube 118 is stationary and as if the orientation of the Earth's magnetic field is changing as a function of gantry angle. In any case, the result can be that the position of the focal-spot (e.g., denoted as focal-spot 310) can change with respect to the reference frame (e.g., with respect to the x-axis and/or y-axis) of the X-ray tube 118, as the X-ray tube 118 rotates about/along the gantry 120.

For example, as shown in FIG. 3, suppose that the Earth's magnetic field interacts with the focal-spot 310 in such a way so as to cause the focal-spot 310 to be positioned slightly right of and significantly below the center of the anode of the X-ray tube 118 (this is a mere non-limiting example for ease of illustration and explanation). As can be seen in FIG. 3, because the Earth's magnetic field can refrain from changing orientation as the X-ray tube 118 rotates about the gantry 120, the focal-spot 310 can maintain its relative position of always being slightly right of and significantly below the center of the anode of the X-ray tube 118. Specifically, the focal-spot 310 can be slightly right of and significantly below the center of the anode of the X-ray tube 118 when the X-ray tube 118 is positioned at the gantry angle 302, when the X-ray tube 118 is positioned at the gantry angle 304, when the X-ray tube 118 is positioned at the gantry angle 306, and/or when the X-ray tube 118 is positioned at the gantry angle 308. However, because the orientation of the X-ray tube 118 can change as the X-ray tube 118 rotates about/along the gantry 120, the reference frame of the X-ray tube 118 can move with respect to the focal-spot 310. From the perspective of the X-ray tube 118, it can be as if the reference frame of the X-ray tube 118 is stationary and as if the focal-spot 310 is moving. Specifically, as shown, when the X-ray tube 118 is located at the gantry angle 302, the position of the focal-spot 310 can be given by a slightly positive x-coordinate and a significantly negative y-coordinate. In contrast, as can be seen, when the X-ray tube 118 is located at the gantry angle 304, the position of the focal-spot 310 can instead be given by a significantly positive x-coordinate and a slightly positive y-coordinate, notwithstanding that the focal-spot 310 is still located slightly rightward of and significantly below the center of the anode of the X-ray tube 118. Furthermore, as shown, when the X-ray tube 118 is located at the gantry angle 306, the position of the focal-spot 310 can be given by a slightly negative x-coordinate and a significantly positive y-coordinate, notwithstanding that the focal-spot 310 is still located slightly rightward of and significantly below the center of the anode of the X-ray tube 118. Further still, as can be seen, when the X-ray tube 118 is located at the gantry angle 308, the position of the focal-spot 310 can instead be given by a significantly negative x-coordinate and a slightly negative y-coordinate, notwithstanding that the focal-spot 310 is still located slightly rightward of and significantly below the center of the anode of the X-ray tube 118.

Therefore, as can be seen in FIG. 3, the focal-spot 310 can be considered as experiencing focal-spot displacement as a function of gantry angle (e.g., the coordinates of the focal-spot 310 with respect to the reference frame of the X-ray tube 118 can change as the X-ray tube 118 rotates about/along the gantry 120). Because the X-ray tube 118 can rotate about/along the gantry 120 during/throughout a medical imaging scan, the motion of the focal-spot 310 can be considered and/or referred to as intra-scan focal-spot displacement. As mentioned above, such intra-scan focal-spot displacement can cause the medical scanner 104 to produce significant imaging artefacts (e.g., shadows, streaks).

Referring back to FIG. 1, it can be desired to operate and/or execute the medical scanner 104 without (and/or with reduced) intra-scan focal-spot displacement. As described herein, the focal-spot compensation system 102 can facilitate such operation and/or execution.

In various embodiments, the focal-spot compensation system 102 can comprise a processor 106 (e.g., computer processing unit, microprocessor) and a computer-readable memory 108 that is operably and/or operatively and/or communicatively connected/coupled to the processor 106. The computer-readable memory 108 can store computer-executable instructions which, upon execution by the processor 106, can cause the processor 106 and/or other components of the focal-spot compensation system 102 (e.g., calibration component 110, receiver component 112, displacement component 114, and/or execution component 116) to perform one or more acts. In various embodiments, the computer-readable memory 108 can store computer-executable components (e.g., calibration component 110, receiver component 112, displacement component 114, and/or execution component 116), and the processor 106 can execute the computer-executable components.

In various embodiments, the focal-spot compensation system 102 can comprise a calibration component 110. In various aspects, as described herein, the calibration component 110 can electronically access, electronically maintain, and/or electronically generate a mapping that is associated with the medical scanner 104. In various cases, the mapping can link and/or correlate anode-cathode voltages and/or gantry angles that can be assumed and/or taken on by the X-ray tube 118 to respective focal-spot displacements.

In various embodiments, the focal-spot compensation system 102 can further comprise a receiver component 112. In various instances, as described herein, the receiver component 112 can electronically receive, retrieve, and/or access a present gantry angle of the X-ray tube 118 and/or a present anode-cathode voltage of the X-ray tube 118.

In various embodiments, the focal-spot compensation system 102 can further comprise a displacement component 114. In various aspects, as described herein, the displacement component 114 can electronically identify a present focal-spot displacement of the X-ray tube 118, by referencing and/or querying the mapping for the present gantry angle and/or the present anode-cathode voltage.

In various embodiments, the focal-spot compensation system 102 can further comprise an execution component 116. In various instances, as described herein, the execution component 116 can electronically control and/or actuate the one or more magnetic dipoles 122, so as to correct, cancel, reduce, and/or otherwise compensate for the present focal-spot displacement.

Figure 4:
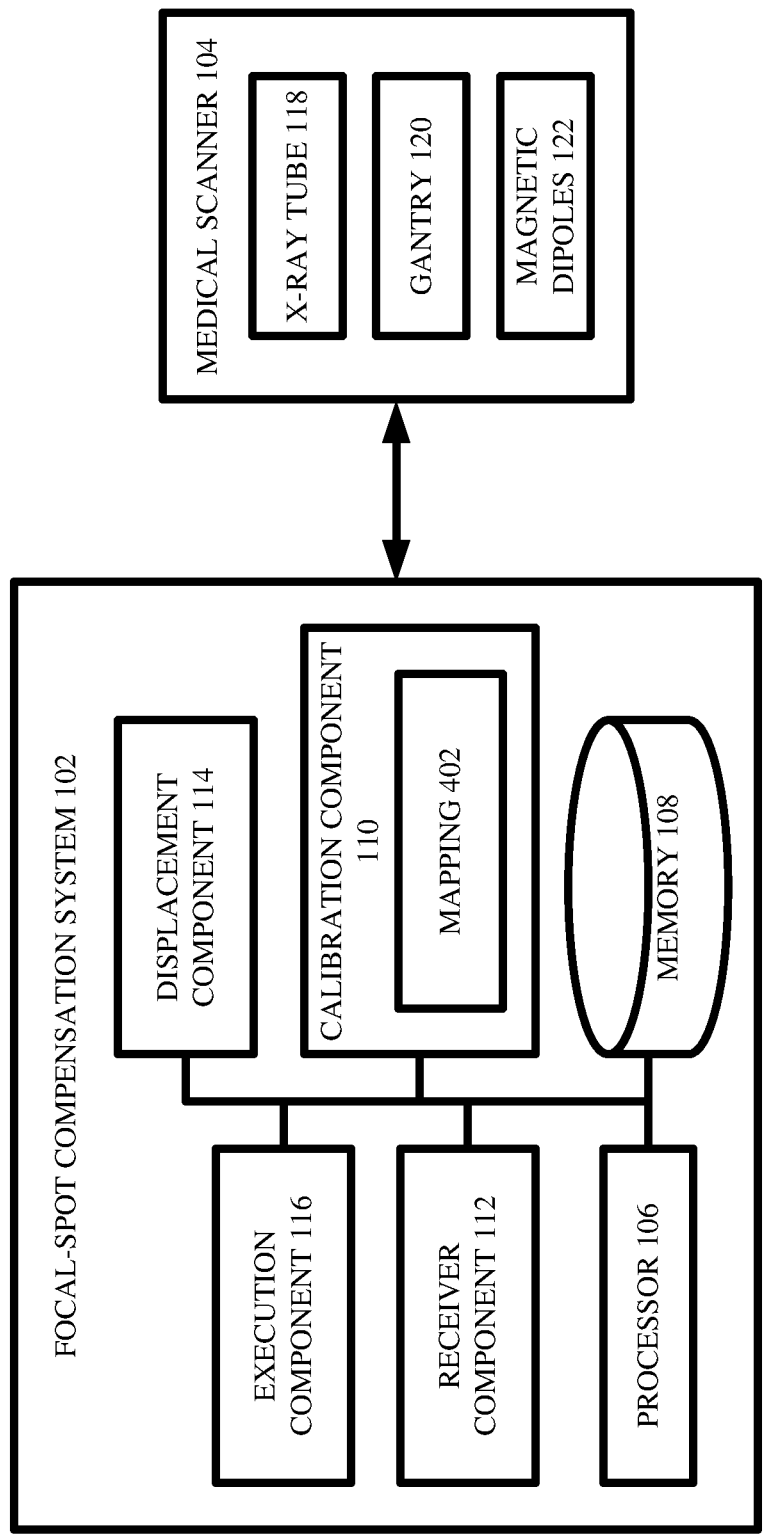
FIG. 4 illustrates a block diagram of an example, non-limiting system including a voltage-angle-displacement mapping that facilitates correction of intra-scan focal-spot displacement in accordance with one or more embodiments described herein.

FIG. 4 illustrates a block diagram of an example, non-limiting system 400 including a voltage-angle-displacement mapping that can facilitate correction of intra-scan focal-spot displacement in accordance with one or more embodiments described herein. As shown, the system 400 can, in some cases, comprise the same components as the system 100, and can further comprise a mapping 402.

In various embodiments, the calibration component 110 can electronically access, electronically store, electronically maintain, and/or electronically generate the mapping 402. In various aspects, the mapping 402 can correspond to and/or be associated with the medical scanner 104. In various cases, the mapping 402 can be any suitable electronic data structure that can correlate and/or otherwise link gantry angles and/or anode-cathode voltages of the X-ray tube 118 to respective focal-spot displacements experienced by the X-ray tube 118. In other words, the mapping 402 can indicate and/or represent how the focal-spot of the X-ray tube 118 changes position in response to different gantry angles and/or in response to different anode-cathode voltages. This is explained with respect to FIG. 5.

Figure 5:
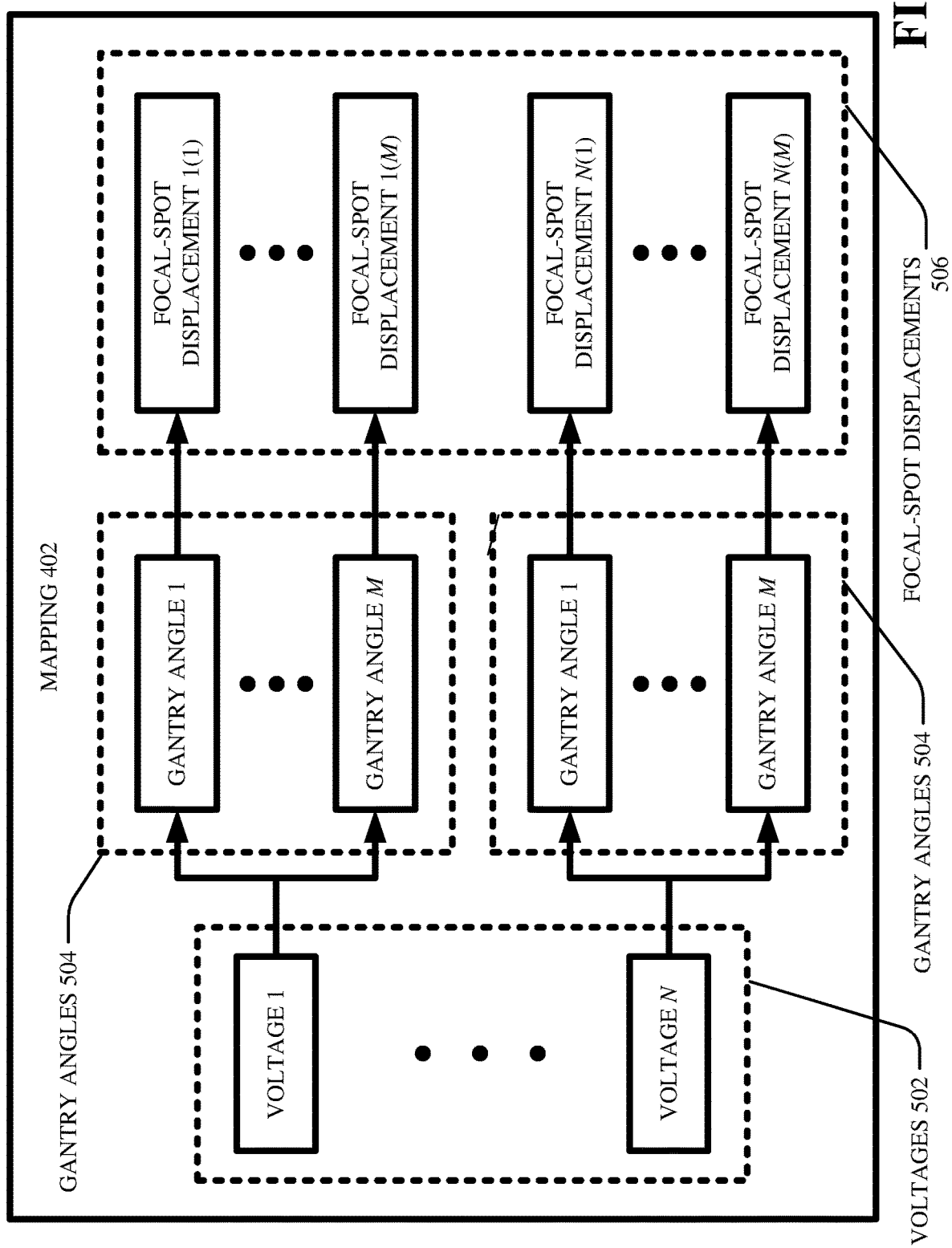
FIG. 5 illustrates an example, non-limiting block diagram showing a voltage-angle-displacement mapping in accordance with one or more embodiments described herein.

FIG. 5 illustrates an example, non-limiting block diagram 500 showing a voltage-angle-displacement mapping in accordance with one or more embodiments described herein. That is, FIG. 5 depicts a non-limiting example embodiment of the mapping 402. As shown, the mapping 402 can include a set of voltages 502, a set of gantry angles 504, and/or a set of focal-spot displacements 506 that respectively correspond to each other.

In various aspects, the set of voltages 502 can include n voltage values (e.g., measured in peak kilovolts) for any suitable positive integer n: a voltage 1 to a voltage n. In various instances, the set of voltages 502 can be considered as representing a range and/or interval of possible discrete voltage values which can be applied by the medical scanner 104 to the anode and/or cathode of the X-ray tube 118. For instance, the voltage 1 can be considered as a scalar that represents a minimum and/or smallest voltage magnitude that can be applied to the anode and/or cathode of the X-ray tube 118 (e.g., application of which can yield a slowest-accelerating electron beam in the X-ray tube 118), and the voltage n can be considered as a scalar that represents a maximum and/or largest voltage magnitude that can be applied to the anode and/or cathode of the X-ray tube 118 (e.g., application of which can yield a fastest-accelerating electron beam in the X-ray tube 118).

In various aspects, the set of gantry angles 504 can include m angle values (e.g., measured in degrees and/or radians) for any suitable positive integer m: a gantry angle 1 to a gantry angle m. In various instances, the set of gantry angles 504 can be considered as representing a range and/or interval of possible discrete positions about/along the gantry 120 where the X-ray tube 118 can be located. For instance, the gantry angle 1 can be considered as a scalar that represents a first position about/along the gantry 120 and to which the X-ray tube 118 can be rotated, and the gantry angle m can be considered as a scalar that represents an m-th position about/along the gantry 120 and to which the X-ray tube 118 can be rotated.

Because the set of voltages 502 can include n voltage values, and because the set of gantry angles 504 can include m angle values, the set of voltages 502 and the set of gantry angles 504 can be considered as collectively forming a total of nm voltage-angle pairs (e.g., also referred to as voltage-angle tuples and/or voltage-angle settings). As described above, the position of the focal-spot of the X-ray tube 118 can change, with respect to the reference frame of the X-ray tube 118, based on gantry angle and/or based on anode-cathode voltage. Accordingly, in various instances, each of the nm voltage-angle pairs can respectively correspond to a unique focal-spot displacement value, thereby yielding a total of nm focal-spot displacements: a focal-spot displacement 1(1) to a focal-spot displacement 1(m), to a focal-spot displacement n(1), to a focal-spot displacement n(m). In various cases, the total of nm focal-spot displacements can be considered as collectively forming the set of focal-spot displacements 506.

For example, the voltage 1 and the gantry angle 1 can be considered as forming a voltage-angle pair, and such voltage-angle pair can respectively correspond to the focal-spot displacement 1(1). In various cases, the focal-spot displacement 1(1) can indicate how far and/or in what direction, with respect to the reference frame of the X-ray tube 118, the Earth's magnetic field causes the focal-spot of the X-ray tube 118 to move away from a desired/predetermined position, when the X-ray tube 118 is configured according to the voltage 1 and the gantry angle 1 (e.g., when the anode and/or cathode of the X-ray tube 118 is exposed to the voltage 1, and when the X-ray tube 118 has been rotated to the gantry angle 1). In cases where the reference frame of the X-ray tube 118 is defined by an x-axis and/or a y-axis, the focal-spot displacement 1(1) can be a two-element vector. A first element of such two-element vector can be a scalar indicating an x-displacement of the focal-spot of the X-ray tube 118 (e.g., can indicate a difference between a predetermined/desired x-position of the focal-spot and an actual x-position which the focal-spot moves to when the X-ray tube 118 is configured according to the voltage 1 and the gantry angle 1). Similarly, a second element of such two-element vector can be a scalar indicating a y-displacement of the focal-spot of the X-ray tube 118 (e.g., can indicate a difference between a predetermined/desired y-position of the focal-spot and an actual y-position which the focal-spot moves to when the X-ray tube 118 is configured according to the voltage 1 and the gantry angle 1).

As another example, the voltage 1 and the gantry angle m can be considered as forming another voltage-angle pair, and such voltage-angle pair can respectively correspond to the focal-spot displacement 1(m). In various cases, the focal-spot displacement 1(m) can indicate how far and/or in what direction, with respect to the reference frame of the X-ray tube 118, the Earth's magnetic field causes the focal-spot of the X-ray tube 118 to move away from a desired/predetermined position, when the X-ray tube 118 is configured according to the voltage 1 and the gantry angle m (e.g., when the anode and/or cathode of the X-ray tube 118 is exposed to the voltage 1, and when the X-ray tube 118 has been rotated to the gantry angle m). In cases where the reference frame of the X-ray tube 118 is defined by an x-axis and/or a y-axis, the focal-spot displacement 1(m) can be a two-element vector. As above, a first element of such two-element vector can be a scalar indicating an x-displacement of the focal-spot of the X-ray tube 118 (e.g., can indicate a difference between a predetermined/desired x-position of the focal-spot and an actual x-position which the focal-spot moves to when the X-ray tube 118 is configured according to the voltage 1 and the gantry angle m). Likewise, a second element of such two-element vector can be a scalar indicating a y-displacement of the focal-spot of the X-ray tube 118 (e.g., can indicate a difference between a predetermined/desired y-position of the focal-spot and an actual y-position which the focal-spot moves to when the X-ray tube 118 is configured according to the voltage 1 and the gantry angle m).

As yet another example, the voltage n and the gantry angle 1 can be considered as forming another voltage-angle pair, and such voltage-angle pair can respectively correspond to the focal-spot displacement n(1). In various cases, the focal-spot displacement n(1) can indicate how far and/or in what direction, with respect to the reference frame of the X-ray tube 118, the Earth's magnetic field causes the focal-spot of the X-ray tube 118 to move away from a desired/predetermined position, when the X-ray tube 118 is configured according to the voltage n and the gantry angle 1 (e.g., when the anode and/or cathode of the X-ray tube 118 is exposed to the voltage n, and when the X-ray tube 118 has been rotated to the gantry angle 1). In cases where the reference frame of the X-ray tube 118 is defined by an x-axis and/or a y-axis, the focal-spot displacement n(1) can be a two-element vector. Just like above, a first element of such two-element vector can be a scalar indicating an x-displacement of the focal-spot of the X-ray tube 118 (e.g., can indicate a difference between a predetermined/desired x-position of the focal-spot and an actual x-position which the focal-spot moves to when the X-ray tube 118 is configured according to the voltage n and the gantry angle 1). Similarly, a second element of such two-element vector can be a scalar indicating a y-displacement of the focal-spot of the X-ray tube 118 (e.g., can indicate a difference between a predetermined/desired y-position of the focal-spot and an actual y-position which the focal-spot moves to when the X-ray tube 118 is configured according to the voltage n and the gantry angle 1).

As still another example, the voltage n and the gantry angle m can be considered as forming yet another voltage-angle pair, and such voltage-angle pair can respectively correspond to the focal-spot displacement n(m). In various cases, the focal-spot displacement n(m) can indicate how far and/or in what direction, with respect to the reference frame of the X-ray tube 118, the Earth's magnetic field causes the focal-spot of the X-ray tube 118 to move away from a desired/predetermined position, when the X-ray tube 118 is configured according to the voltage n and the gantry angle m (e.g., when the anode and/or cathode of the X-ray tube 118 is exposed to the voltage n, and when the X-ray tube 118 has been rotated to the gantry angle m). In cases where the reference frame of the X-ray tube 118 is defined by an x-axis and/or a y-axis, the focal-spot displacement n(m) can be a two-element vector. Again, a first element of such two-element vector can be a scalar indicating an x-displacement of the focal-spot of the X-ray tube 118 (e.g., can indicate a difference between a predetermined/desired x-position of the focal-spot and an actual x-position which the focal-spot moves to when the X-ray tube 118 is configured according to the voltage n and the gantry angle m). Likewise, a second element of such two-element vector can be a scalar indicating a y-displacement of the focal-spot of the X-ray tube 118 (e.g., can indicate a difference between a predetermined/desired y-position of the focal-spot and an actual y-position which the focal-spot moves to when the X-ray tube 118 is configured according to the voltage n and the gantry angle m).

In various aspects, the mapping 402 can be electronically generated (e.g., via the calibration component 110) based on one or more experiments conducted with respect to the medical scanner 104. For example, as mentioned above, the mapping 402 can include a total of nm voltage-angle pairs. In various aspects, the X-ray tube 118 of the medical scanner 104 can be swept through (e.g., can be sequentially configured according to) each of such nm voltage-angle pairs. For each voltage-angle pair that is swept by the X-ray tube 118, a respectively corresponding focal-spot displacement can be measured (e.g., via any suitable tungsten edge measurement technique). In this way, a total of nm measured focal-spot displacements can be obtained (e.g., one measured focal-spot displacement per voltage-angle pair). This is further explained with respect to FIG. 6.

Figure 6:
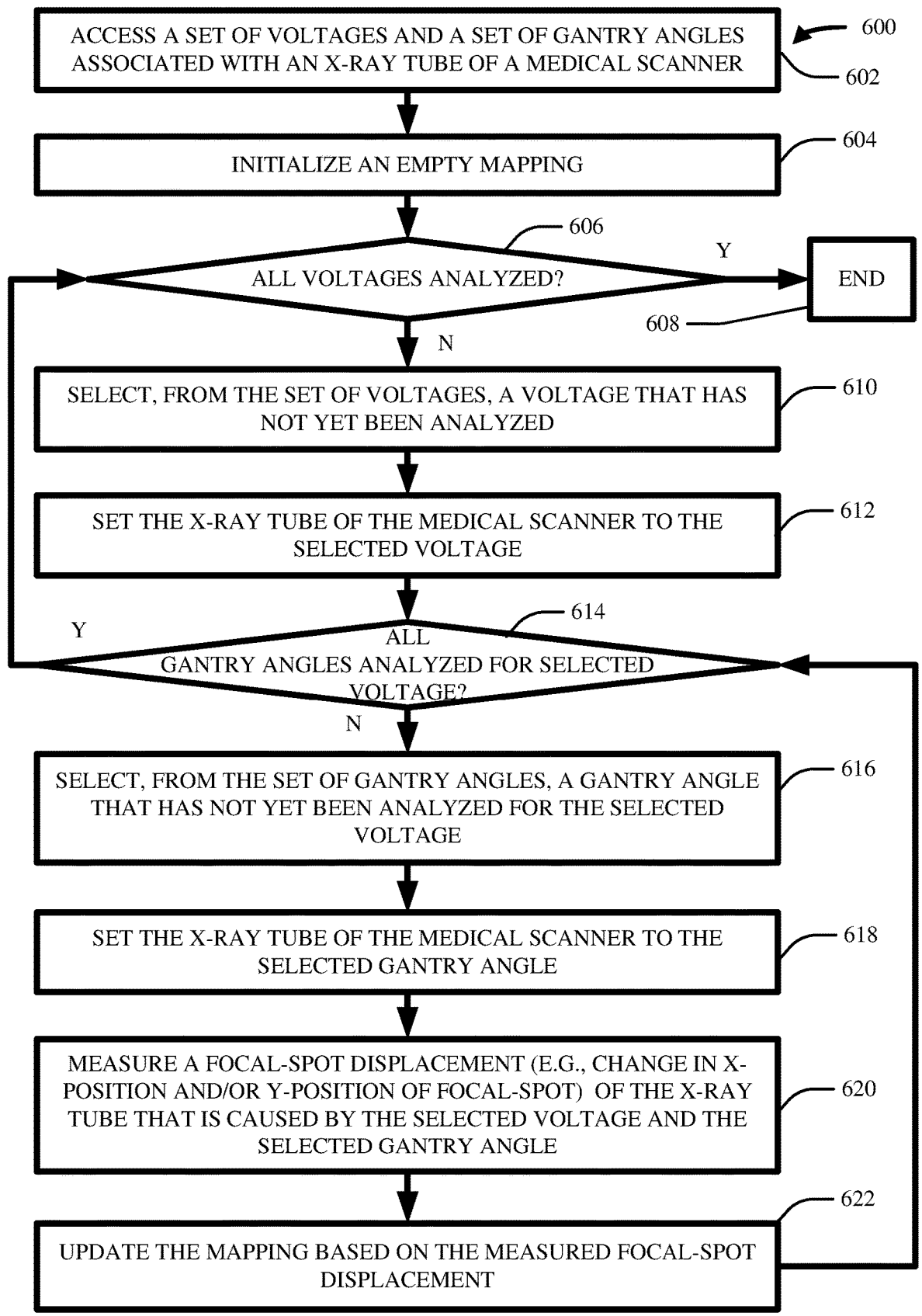
FIG. 6 illustrates an example, non-limiting flow diagram showing how a voltage-angle-displacement mapping can be generated in accordance with one or more embodiments described herein.

FIG. 6 illustrates an example, non-limiting flow diagram 600 showing how a voltage-angle-displacement mapping can be generated in accordance with one or more embodiments described herein. That is, FIG. 6 shows how the mapping 402 can be created in various embodiments.

In various aspects, act 602 can include accessing a set of voltages (e.g., 502) and/or a set of gantry angles (e.g., 504) associated with an X-ray tube (e.g., 118), of a medical scanner (e.g., 104).

In various instances, act 604 can include initializing an empty mapping (e.g., 402 can be initially empty).

In various cases, act 606 can include determining whether all voltages in the set of voltages have been analyzed yet (e.g., whether all voltages in the set of voltages have been used to update the mapping yet). If so, the flow-diagram 600 can proceed to act 608 where it can end (e.g., the mapping can be considered as complete at this point). If not, the flow-diagram 600 can instead proceed to act 610.

In various aspects, act 610 can include selecting, from the set of voltages, a voltage that has not yet been analyzed (e.g., that has not yet been used to update the mapping).

In various instances, act 612 can include setting and/or configuring the X-ray tube of the medical scanner to the selected voltage (e.g., applying the selected voltage to the anode and/or cathode of the X-ray tube).

In various cases, act 614 can include determining whether all gantry angles in the set of gantry angles have been analyzed yet for the selected voltage (e.g., whether all gantry angles in the set of gantry angles have yet been used to update the mapping in conjunction and/or combination with the selected voltage). If so, the flow-diagram 600 can proceed back to act 606. If not, the flow-diagram 600 can instead proceed to act 616.

In various aspects, act 616 can include selecting, from the set of gantry angles, a gantry angle that has not yet been analyzed for the selected voltage (e.g., that has not yet been used to update the mapping in conjunction and/or combination with the selected voltage).

In various instances, act 618 can include setting and/or configuring the X-ray tube of the medical scanner to the selected gantry angle (e.g., rotating the X-ray tube to a position/location defined by the selected gantry angle).

In various cases, act 620 can include measuring a focal-spot displacement (e.g., a change in x-position and/or a change in y-position of the focal-spot) of the X-ray tube that can be caused by the selected voltage and/or the selected gantry angle. In other words, act 620 can include measuring how far and/or in what direction the focal-spot moves from a predetermined/desired position, where such motion of the focal-spot can be caused by and/or can be in response to the X-ray tube being placed at the selected gantry angle and/or to the anode and cathode of the X-ray tube being exposed to the selected voltage. As those having ordinary skill in the art will appreciate, any suitable measurement technique can be implemented, such as a tungsten edge technique.

In various aspects, act 622 can include updating the mapping based on the measured focal-spot displacement (e.g., editing the mapping, so that the mapping now indicates that the selected voltage and the selected gantry angle together cause and/or are correlated with the measured focal-spot displacement). As shown, the flow-diagram 600 can then proceed back to act 614.

As shown, acts 614-622 can iterate until all gantry angles have been used in conjunction with the selected voltage. Those having ordinary skill in the art will appreciate that this can be considered as sweeping the set of gantry angles. Moreover, as shown, act 606-614 can iterate until all voltages have been used to update the mapping. Those having ordinary skill in the art will appreciate that this can be considered as sweeping the set of voltages. Although FIG. 6 illustrates the set of gantry angles being swept for each voltage, this is a mere non-limiting example. In some cases, the order of sweeping can be inverted (e.g., a gantry angle can be selected first, and then the set of voltages can be swept for that selected gantry angle).

In any case, the mapping 402 can be generated by measuring how the focal-spot of the X-ray tube 118 responds to real-world gantry angle rotations and/or to real-world anode-cathode voltages. Accordingly, the mapping 402 can, in various instances, be considered as a look-up table that indicates how the focal-spot of the X-ray tube 118 moves in response to and/or as a function of gantry angle and/or anode-cathode voltage.

Figure 7:
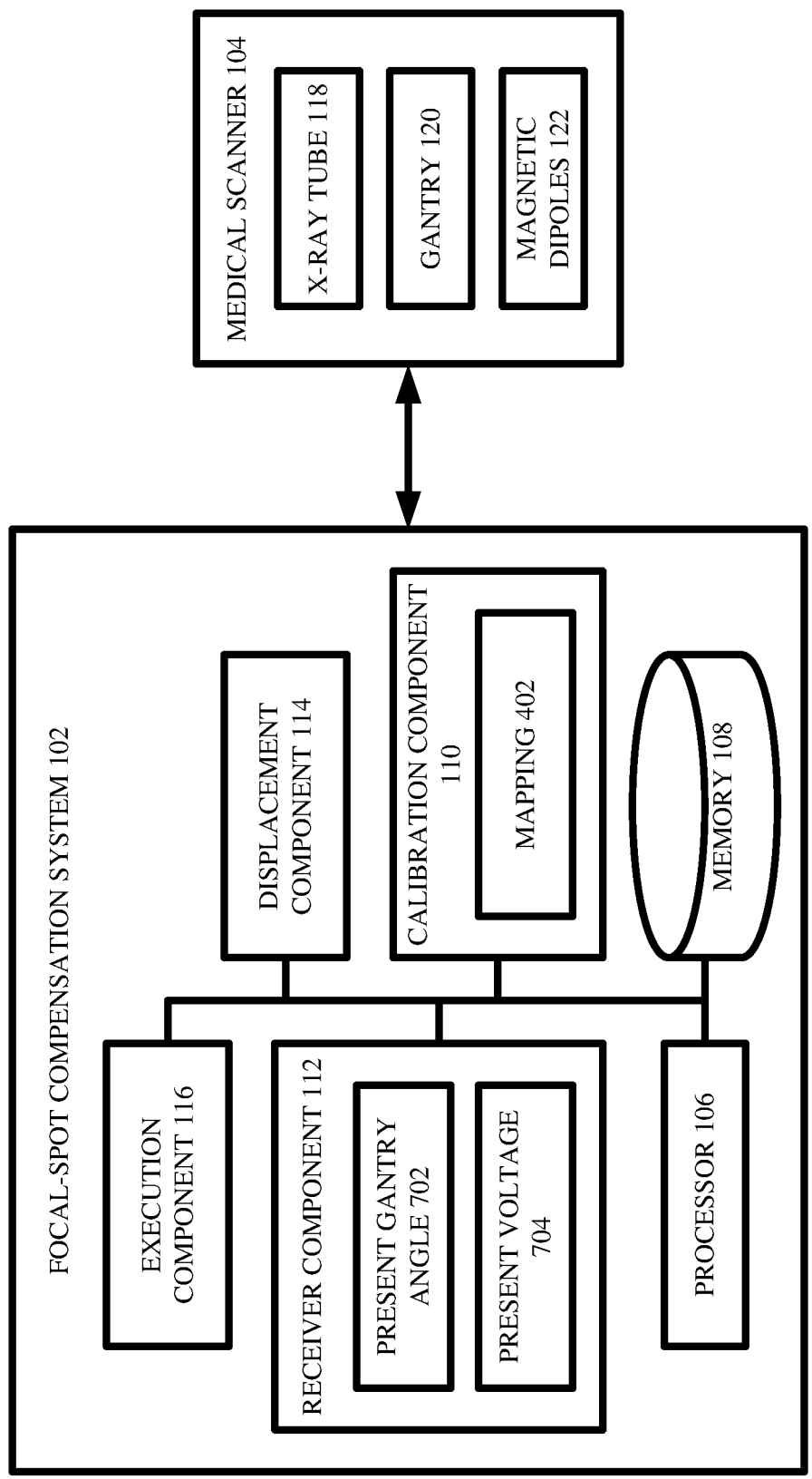
FIG. 7 illustrates a block diagram of an example, non-limiting system including a present gantry angle and/or a present voltage that facilitates correction of intra-scan focal-spot displacement in accordance with one or more embodiments described herein.

FIG. 7 illustrates a block diagram of an example, non-limiting system 700 including a present gantry angle and/or a present voltage that can facilitate correction of intra-scan focal-spot displacement in accordance with one or more embodiments described herein. As shown, the system 700 can, in some cases, comprise the same components as the system 400, and can further comprise a present gantry angle 702 and/or a present voltage 704.

In various embodiments, the receiver component 112 can electronically receive and/or otherwise electronically access the present gantry angle 702 and/or the present voltage 704. In various instances, the receiver component 112 can electronically retrieve the present gantry angle 702 and/or the present voltage 704 from any suitable centralized and/or decentralized data structure (not shown). In various other instances, the receiver component 112 can electronically retrieve the present gantry angle 702 and/or the present voltage 704 from the medical scanner 104 itself (e.g., from a control module of the medical scanner 104, and/or from position sensors and/or voltage sensors of the medical scanner 104). In any case, the receiver component 112 can electronically obtain and/or access the present gantry angle 702 and/or the present voltage 704, such that other components of the focal-spot compensation system 102 can electronically interact with the present gantry angle 702 and/or the present voltage 704.

In various aspects, the present gantry angle 702 can be any suitable scalar that indicates a gantry angle at which the X-ray tube 118 is currently/presently positioned, and/or that indicates a gantry angle to which the X-ray tube 118 is desired to be rotated. Similarly, in various instances, the present voltage 704 can be any suitable scalar that indicates a voltage level that is currently/presently being applied to the anode and cathode of the X-ray tube 118, and/or that indicates a voltage level which is desired to be applied to the anode and cathode of the X-ray tube 118.

Figure 8:
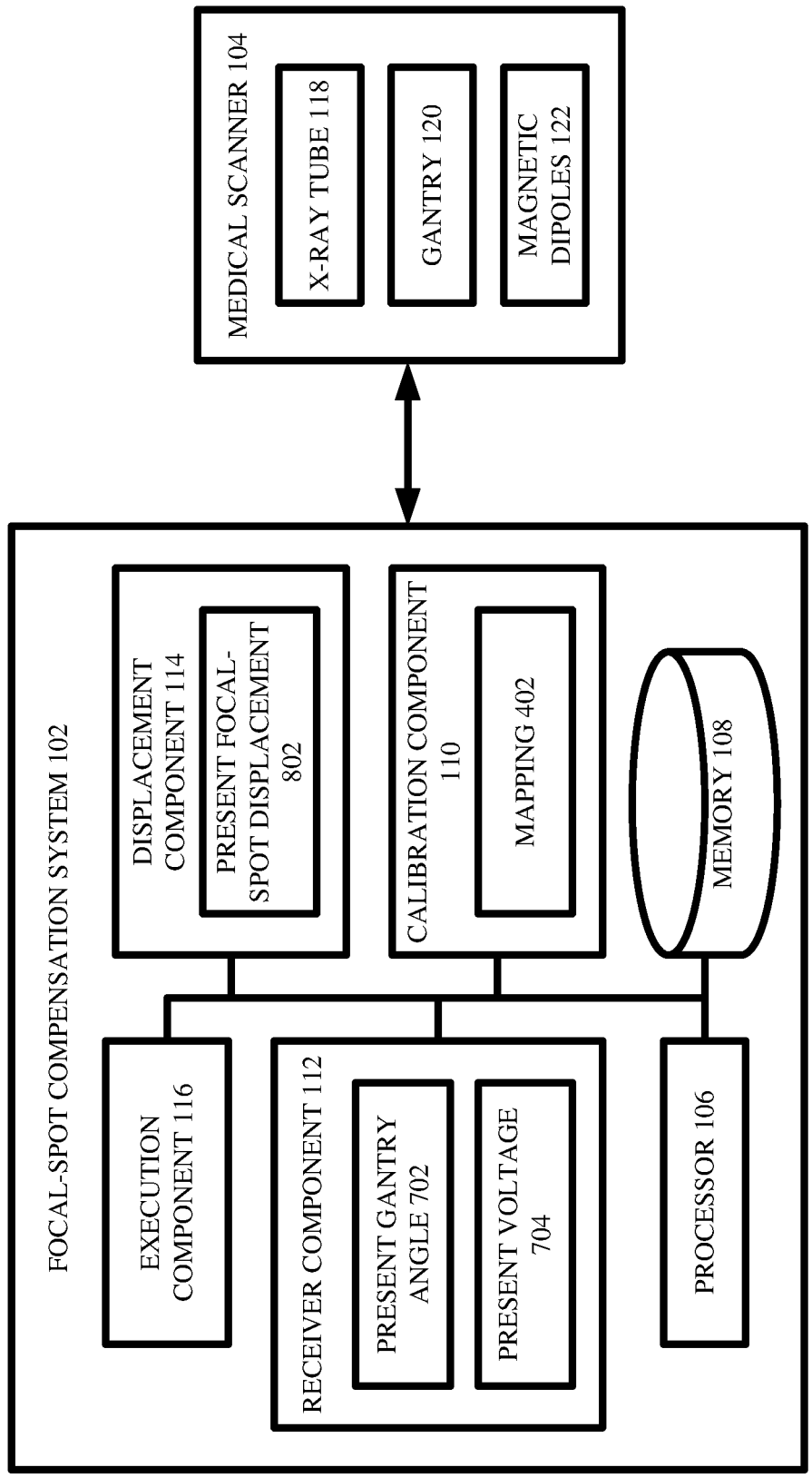
FIG. 8 illustrates a block diagram of an example, non-limiting system including a present focal-spot displacement that facilitates correction of intra-scan focal-spot displacement in accordance with one or more embodiments described herein.

FIG. 8 illustrates a block diagram of an example, non-limiting system 800 including a present focal-spot displacement that can facilitate correction of intra-scan focal-spot displacement in accordance with one or more embodiments described herein. As shown, the system 800 can, in some cases, comprise the same components as the system 700, and can further comprise a present focal-spot displacement 802.

In various embodiments, the displacement component 114 can electronically determine and/or identify the present-focal spot displacement 802 based on the present gantry angle 702 and/or based on the present voltage 704, by referencing the mapping 402. More specifically, as explained herein, the mapping 402 can be considered as correlating voltage-angle pairs to focal-spot displacements. Moreover, the present gantry angle 702 and/or the present voltage 704 can be considered as collectively forming a voltage-angle pair. Accordingly, the displacement component 114 can electronically search and/or query the mapping 402 for a voltage-angle pair that matches the present gantry angle 702 and/or the present voltage 704, and the mapping 402 can indicate and/or specify a focal-spot displacement that is correlated/linked with such voltage-angle pair. In various cases, that focal-spot displacement that is identified/found in the mapping 402 can be considered as the present focal-spot displacement 802. In other words, the present focal-spot displacement 802 can be considered as indicating how the focal-spot of the X-ray tube 118 has and/or can be expected to move, in response to the X-ray tube 118 being configured/set to the present gantry angle 702 and/or to the present voltage 704.

In various embodiments, the execution component 116 can electronically adjust, manipulate, and/or otherwise control the one or more magnetic dipoles 122, so as to correct, cancel, and/or otherwise compensate for the present focal-spot displacement 802. In particular, as explained above, those having ordinary skill in the art will appreciate how the one or more magnetic dipoles 122 can be controlled so as to steer the focal-spot of the X-ray tube 118 in a desired direction by a desired distance. Accordingly, in various instances, when the present focal-spot displacement 802 is known, the execution component 116 can electronically control the one or more magnetic dipoles 122 (e.g., can electronically control one or more electromagnets that generate/create/emit the one or more magnetic dipoles 122) so as to cause the focal-spot of the X-ray tube 118 to move back and/or closer to a predetermined/desired location. In some cases, the one or more magnetic dipoles 122 can be adjusted/manipulated so as to cause the focal-spot to move in a direction opposite to a direction indicated by the present focal-spot displacement 802, and/or so as to cause the focal-spot to move by a distance that is equal to and/or otherwise based on the magnitude of the present focal-spot displacement 802. As a non-limiting example, suppose that the present focal-spot displacement 802 indicates that the present gantry angle 702 and the present voltage 704 have caused and/or will cause the focal-spot of the X-ray tube 118 to have an x-displacement of q microns for any suitable real-number q and a y-displacement of r microns for any suitable real-number r. That is, the present gantry angle 702 and the present voltage 704 can cause the focal-spot to be q microns away from the predetermined/desired x-position and to be r microns away from the predetermined/desired y-position. In such case, the execution component 116 can electronically alter/adjust the one or more magnetic dipoles 122, so as to cause the x-position of the focal-spot to change by −q microns and/or so as to cause the y-position of the focal-spot to change by −r microns. As those having ordinary skill in the art will appreciate, if q is positive, then −q can cause the focal-spot to move in the negative direction along the x-axis. Conversely, if q is negative, then −q can cause the focal-spot to move in the positive direction along the x-axis. Likewise, if r is positive, then −r can cause the focal-spot to move in the negative direction along the y-axis. Conversely, if r is negative, then −r can cause the focal-spot to move in the positive direction along the y-axis.

In any case, the execution component 116 can electronically adjust the one or more magnetic dipoles 122, so as to move the focal-spot of the X-ray tube 118 in a direction and/or by an amount that counteracts the present focal-spot displacement 802.

In various aspects, if the X-ray tube 118 is not already set/configured to the present gantry angle 702 and/or the present voltage 704, then the execution component 116 can electronically cause the X-ray tube 118 to become set/configured according to the present gantry angle 702 and/or the present voltage 704 (e.g., can instruct/command the X-ray tube 118 to rotate to a position about/along the gantry 120 that is given by the present gantry angle 702, can instruct/command the X-ray tube 118 to apply the present voltage 704 to its anode and/or cathode).

In various aspects, the above-described functionalities of the receiver component 112, the displacement component 114, and/or the execution component 116 can help to ameliorate displacement of the focal-spot of the X-ray tube 118 that is caused by a single voltage-angle pair (e.g., that is caused by the present gantry angle 702 and/or the present voltage 704). In various cases, however, such functionalities can be repeated for any suitable number of voltage-angle pairs. For example, if a medical imaging scan (e.g., a scanning protocol) of the medical scanner 104 involves sweeping the X-ray tube 118 through a plurality of voltage-angle pairs, then the functionalities of the receiver component 112, the displacement component 114, and/or the execution component 116 can be repeated for each of such plurality of voltage-angle pairs. The ultimate result of such repetition can be that the focal-spot of the X-ray tube 118 does not deviate (e.g., and/or only deviates very little, within any suitable threshold margin and/or resolution) from its predetermined/desired position during/throughout the medical imaging scan. In other words, such functionalities can help to reduce and/or eliminate intra-scan focal-spot displacement of the medical scanner 104. This is further explained with respect to FIG. 9.

Figure 9:
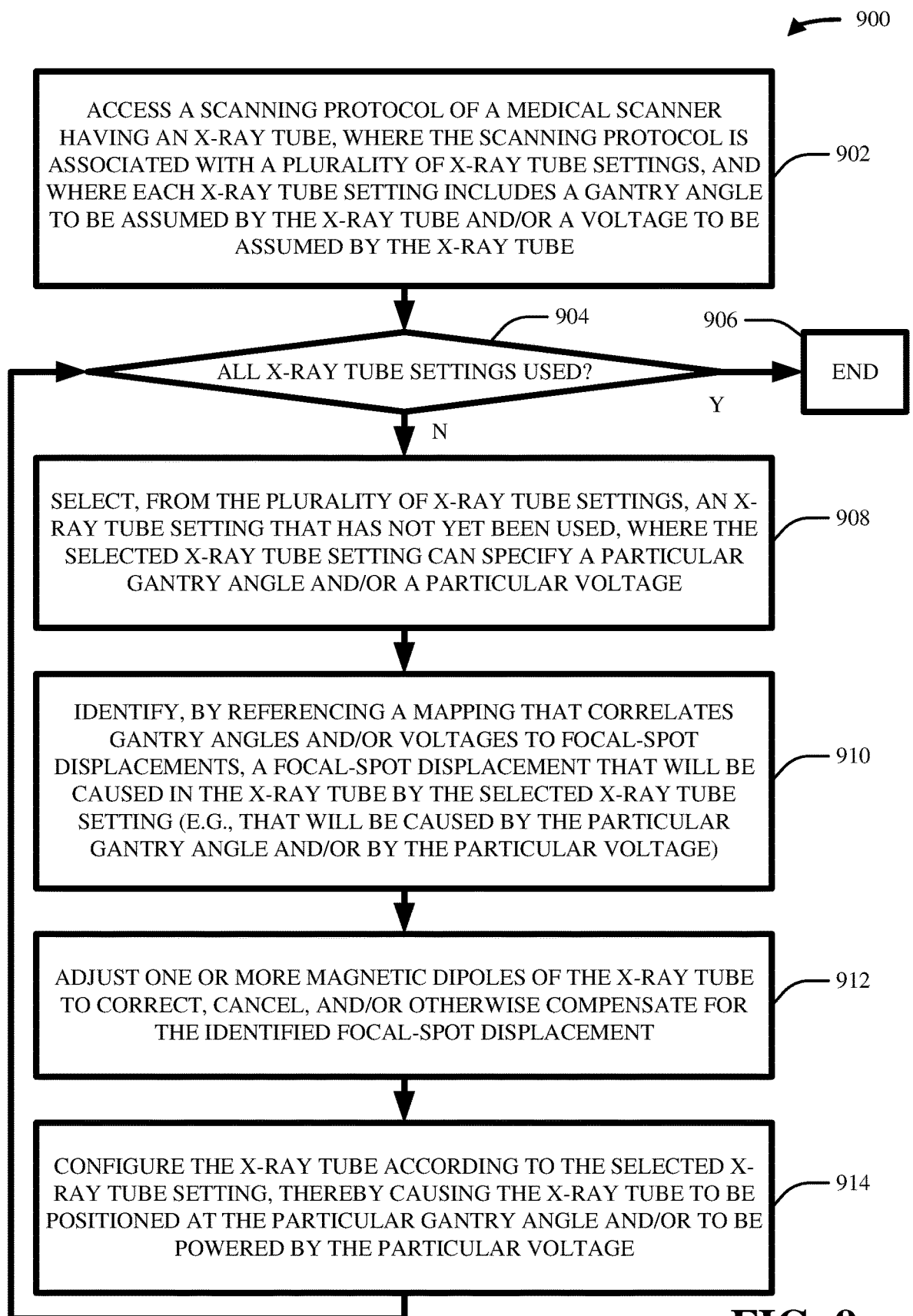
FIG. 9 illustrates a flow diagram of an example, non-limiting computer-implemented method that facilitates correction of intra-scan focal-spot displacement in accordance with one or more embodiments described herein.

FIG. 9 illustrates a flow diagram of an example, non-limiting computer-implemented method 900 that can facilitate correction of intra-scan focal-spot displacement in accordance with one or more embodiments described herein. In various cases, the focal-spot compensation system 102 can facilitate and/or implement the computer-implemented method 900.

In various embodiments, act 902 can include accessing, by a device (e.g., via 112) operatively coupled to a processor, a scanning protocol of a medical scanner (e.g., 104) having an X-ray tube (e.g., 118). In various cases, the scanning protocol can be associated with a plurality of X-ray tube setting, with each X-ray tube setting specifying a gantry angle to be assumed by the X-ray tube and/or an anode-cathode voltage to be assumed by the X-ray tube. In other words, each X-ray tube setting can be considered as a voltage-angle pair.

In various aspects, act 904 can include determining, by the device (e.g., via 112), whether all X-ray tube settings in the plurality of X-ray tube settings have yet been used during the scanning protocol. If so, the computer-implemented method 900 can proceed to act 906, where it can end (e.g., at this point, the X-ray tube can be considered as having swept through each X-ray tube setting in the plurality of X-ray tube settings, and thus the scanning protocol can be considered as complete/finished). If not, the computer-implemented method 900 can instead proceed to act 908.

In various instances, act 908 can include selecting, by the device (e.g., via 112) and from the plurality of X-ray tube settings, an X-ray tube setting that has not yet been used during the scanning protocol. In various cases, the selected X-ray tube setting can specify a particular gantry angle (e.g., 702) and/or a particular anode-cathode voltage (e.g., 704) to which the X-ray tube is supposed to be configured.

In various aspects, act 910 can include identifying, by the device (e.g., via 114) and by referencing a mapping (e.g., 402) that correlates gantry angles and/or anode-cathode voltages to focal-spot displacements, a focal-spot displacement (e.g., 802) that is and/or will be caused in the X-ray tube by the selected X-ray tube setting (e.g., that is and/or will be caused by configuring the X-ray tube according to the particular gantry angle and/or the particular anode-cathode voltage).

In various instances, act 912 can include adjusting, by the device (e.g., via 116), one or more magnetic dipoles (e.g., 122) of the X-ray tube, so as to correct, cancel, and/or otherwise compensate for the identified focal-spot displacement. In other words, the one or more magnetic dipoles can be controllably manipulated, and such controlled manipulation can cause the focal-spot of the X-ray tube to move in a direction opposite to that of the identified focal-spot displacement and/or by a distance that is equal to a magnitude of the identified focal-spot displacement.

In various aspects, act 914 can include configuring, by the device (e.g., via 116), the X-ray tube according to the selected X-ray tube setting, thereby causing the X-ray tube to be positioned at the particular gantry angle and/or to be powered by the particular anode-cathode voltage. In various instances, the computer-implemented method 900 can then proceed back to act 904.

Figure 10:
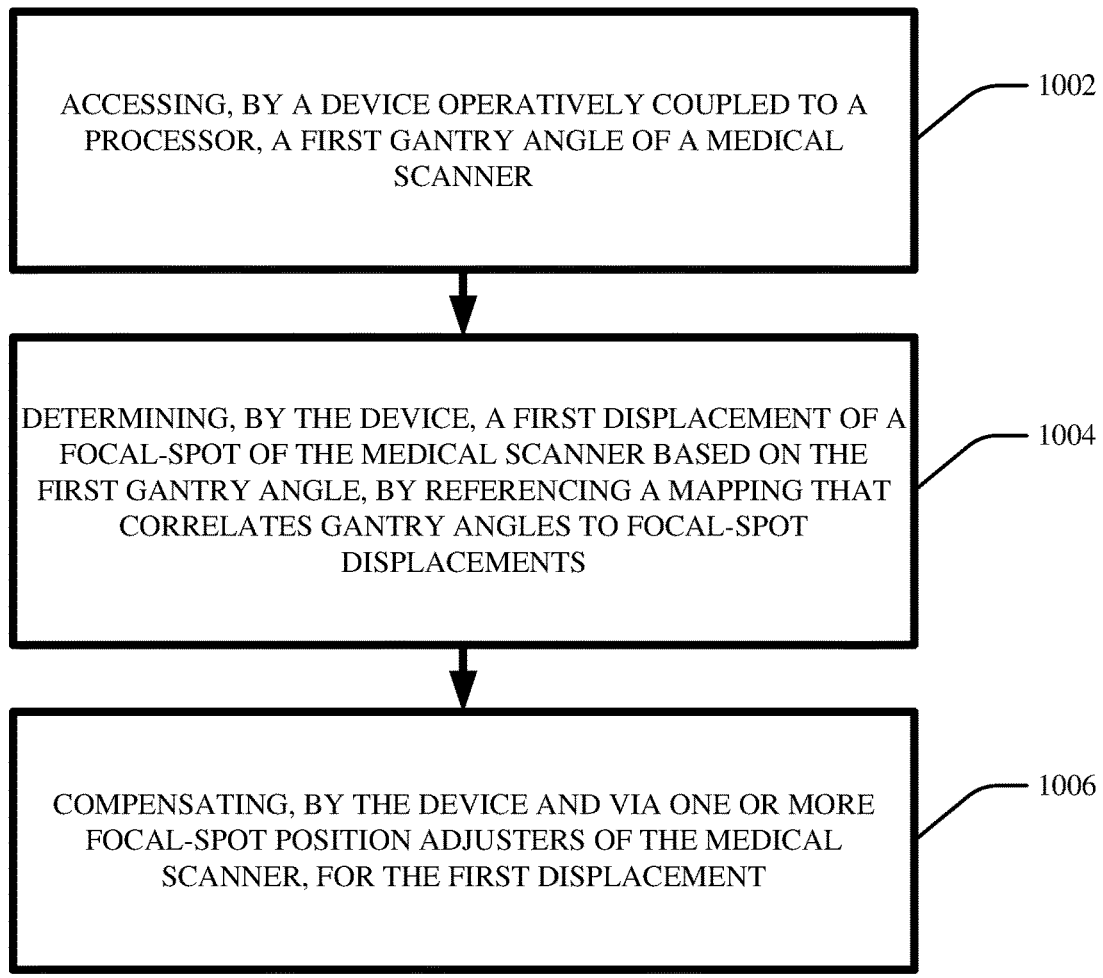
FIG. 10 illustrates a flow diagram of an example, non-limiting computer-implemented method that facilitates correction of intra-scan focal-spot displacement in accordance with one or more embodiments described herein.

FIG. 10 illustrates a flow diagram of an example, non-limiting computer-implemented method 1000 that can facilitate correction of intra-scan focal-spot displacement in accordance with one or more embodiments described herein. In various cases, the focal-spot compensation system 102 can facilitate and/or perform the computer-implemented method 1000.

In various embodiments, act 1002 can include accessing, by a device (e.g., via 112) operatively coupled to a processor, a first gantry angle (e.g., 702) of a medical scanner (e.g., 104).

In various aspects, act 1004 can include determining, by the device (e.g., via 114), a first displacement (e.g., 802) of a focal-spot of the medical scanner based on the first gantry angle, by referencing a mapping (e.g., 402) that correlates gantry angles (e.g., 504) to focal-spot displacements (e.g., 506).

In various instances, act 1006 can include compensating, by the device (e.g., via 116) and via one or more focal-spot position adjusters (e.g., 122) of the medical scanner, for the first displacement.

Although not explicitly shown in FIG. 10, the computer-implemented method 1000 can further include: accessing, by the device (e.g., via 112), a first voltage level (e.g., 704) of the medical scanner, wherein the mapping further correlates voltage levels (e.g., 502) to focal-spot displacements; and determining, by the device (e.g., via 114), the first displacement of the focal-spot of the medical scanner based on the first voltage level.

Although not explicitly shown in FIG. 10, the computer-implemented method 1000 can further include generating, by the device (e.g., via 110), the mapping by: sweeping, by the device (e.g., via 110), the medical scanner through a plurality of gantry angles; and measuring, by the device (e.g., via 110) and at each of the plurality of gantry angles, how far and in what direction the focal-spot of the medical scanner has drifted from a predetermined position (e.g., as shown with respect to FIG. 6).

Although not explicitly shown in FIG. 10, the one or more focal-spot position adjusters can cause the focal-spot to move in an opposite direction as the first displacement, and the one or more focal-spot position adjusters can cause the focal-spot to move by a distance that is equal to (and/or otherwise based on) a magnitude of the first displacement.

Although not explicitly shown in FIG. 10, the one or more focal-spot position adjusters of the medical scanner can be magnetic dipoles or electrostatic deflection electrodes.

Although not explicitly shown in FIG. 10, the medical scanner can be a computed tomography scanner or a tomosynthesis mammography scanner.

Although not explicitly shown in FIG. 10, the computer-implemented method 1000 can further include: accessing, by the device (e.g., via 112), a second gantry angle of the medical scanner after the compensating for the first displacement; determining, by the device (e.g., via 114), a second displacement of the focal-spot of the medical scanner based on the second gantry angle, by referencing the mapping that correlates gantry angles to focal-spot displacements; and compensating, by the device (e.g., via 116) and via the one or more focal-spot position adjusters of the medical scanner, for the second displacement (e.g., as shown with respect to FIG. 9).

Therefore, various embodiments described herein pertain to a computerized tool that can reduce and/or ameliorate intra-scan focal-spot displacement. More specifically, for a medical scanner having an X-ray tube that can rotate about/along a gantry and which is equipped with controllable magnetic dipoles, the present inventors realized that intra-scan focal-spot displacement can be caused by maintaining the controllable magnetic dipoles at constant/uniform parameters. Moreover, the present inventors realized that intra-scan focal-spot displacement can be reduced by not maintaining the controllable magnetic dipoles at constant/uniform parameters. In other words, the present inventors realized that intra-scan focal-spot displacement can be remedied by continually adjusting the parameters of the controllable magnetic dipoles as a function of gantry angle and/or as a function of anode-cathode voltage (e.g., rather than holding the parameters of the magnetic dipoles constant across all gantry angles and/or across all anode-cathode voltages, the parameters of the magnetic dipoles can be uniquely adjusted for each unique voltage-angle pair). A computerized tool that can help to solve the problem of intra-scan focal-spot displacement in such way certainly qualifies as a useful and practical application of computers.

Those having ordinary skill in the art will appreciate that various embodiments described herein can be applied to wobble and/or non-wobble medical imaging devices as desired. For example, for a non-wobble medical imaging device, it can be desired to keep the focal-spot at a single desired position throughout a scan. In contrast, for a wobble medical imaging device, it can be desired to alternate the focal-spot between two or more desired positions throughout a scan. In any of these cases, the herein described teachings can be applied so as to eliminate/reduce intra-scan focal-spot displacement. More specifically, at any given point in time, the focal-spot of a medical imaging scanner can experience some amount of displacement from a desired/predetermined position, where such displacement can be caused by the gantry angle and/or the anode-cathode voltage of the medical imaging device. If the medical imaging device exhibits a non-wobble configuration, then that desired/predetermined position can be the same and/or can be constant for all points in time. On the other hand, if the medical imaging device exhibit a wobble configuration, then that desired/predetermined position can be not constant and/or non-uniform for all points in time (e.g., at a given point in time, it can be desired to place the focal-spot in a given location; at a different point in time, it can be desired to place the focal-spot in a different location). In any case, whatever the desired location of the focal-spot is at a particular point in time, an amount of displacement from that desired location can be determined/measured as described herein, and such amount of displacement can be remedied/corrected as described herein.

In various instances, machine learning algorithms and/or models can be implemented in any suitable way to facilitate any suitable aspects described herein. To facilitate some of the above-described machine learning aspects of various embodiments of the subject innovation, consider the following discussion of artificial intelligence (AI). Various embodiments of the present innovation herein can employ artificial intelligence to facilitate automating one or more features of the present innovation. The components can employ various AI-based schemes for carrying out various embodiments/examples disclosed herein. In order to provide for or aid in the numerous determinations (e.g., determine, ascertain, infer, calculate, predict, prognose, estimate, derive, forecast, detect, compute) of the present innovation, components of the present innovation can examine the entirety or a subset of the data to which it is granted access and can provide for reasoning about or determine states of the system and/or environment from a set of observations as captured via events and/or data. Determinations can be employed to identify a specific context or action, or can generate a probability distribution over states, for example. The determinations can be probabilistic; that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether or not the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, and so on)) schemes and/or systems (e.g., support vector machines, neural networks, expert systems, Bayesian belief networks, fuzzy logic, data fusion engines, and so on) in connection with performing automatic and/or determined action in connection with the claimed subject matter. Thus, classification schemes and/or systems can be used to automatically learn and perform a number of functions, actions, and/or determinations.

A classifier can map an input attribute vector, $z=(z_1, z_2, z_3, z_4, z_n)$, to a confidence that the input belongs to a class, as by $f(z)=confidence(class)$. Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence, any of which can be employed. Classification as used herein also is inclusive of statistical regression that is utilized to develop models of priority.

Those having ordinary skill in the art will appreciate that the herein disclosure describes non-limiting examples of various embodiments of the subject innovation. For ease of description and/or explanation, various portions of the herein disclosure utilize the term "each" when discussing various embodiments of the subject innovation. Those having ordinary skill in the art will appreciate that such usages of the term "each" are non-limiting examples. In other words, when the herein disclosure provides a description that is applied to "each" of some particular object and/or component, it should be understood that this is a non-limiting example of various embodiments of the subject innovation, and it should be further understood that, in various other embodiments of the subject innovation, it can be the case that such description applies to fewer than "each" of that particular object and/or component.

Figure 11:
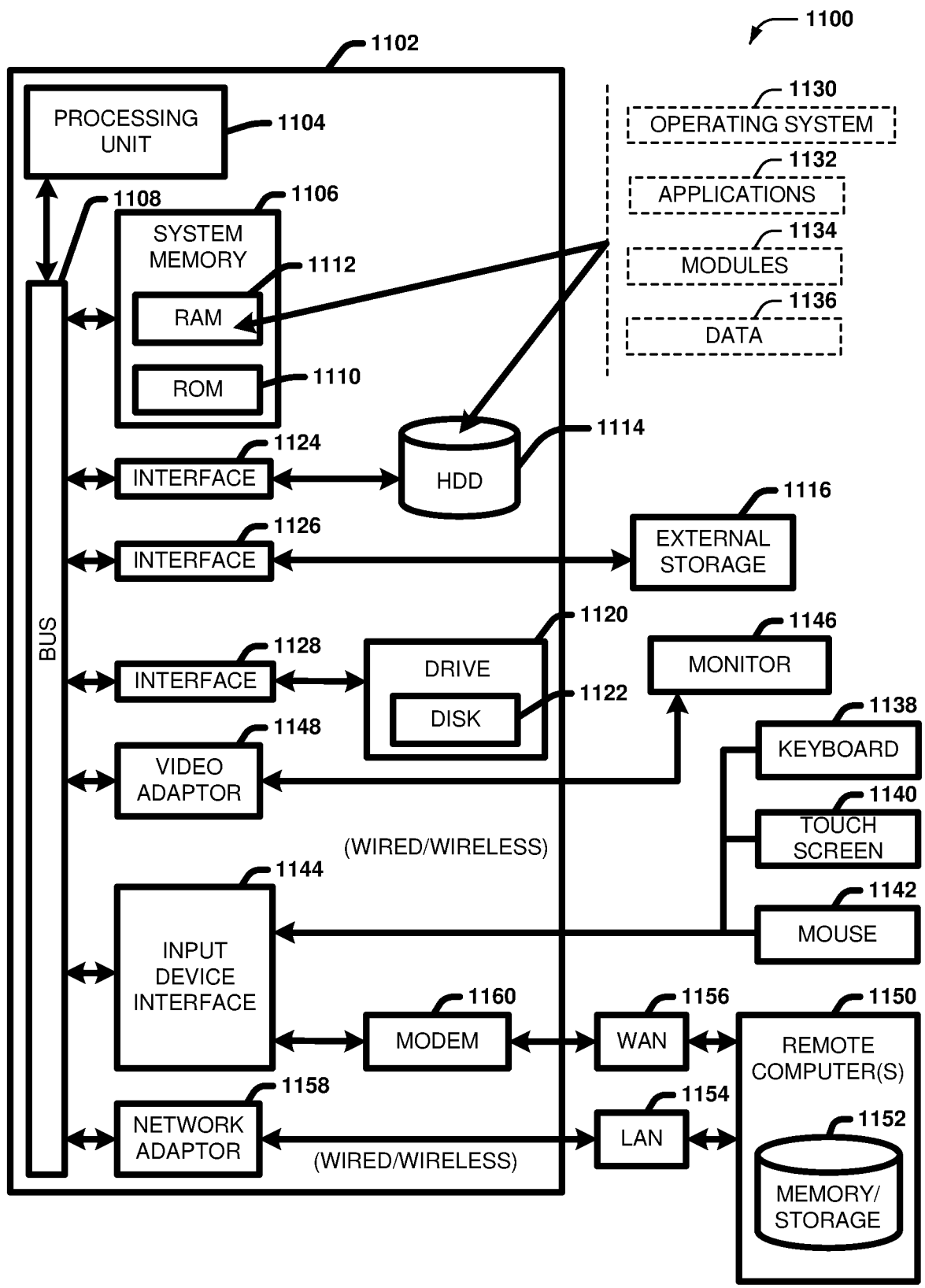
FIG. 11 illustrates a block diagram of an example, non-limiting operating environment in which one or more embodiments described herein can be facilitated.

In order to provide additional context for various embodiments described herein, FIG. 11 and the following discussion are intended to provide a brief, general description of a suitable computing environment 1100 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multi-processor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 11, the example environment 1100 for implementing various embodiments of the aspects described herein includes a computer 1102, the computer 1102 including a processing unit 1104, a system memory 1106 and a system bus 1108. The system bus 1108 couples system components including, but not limited to, the system memory 1106 to the processing unit 1104. The processing unit 1104 can be any of various commercially available processors. Dual microprocessors and other multi-processor architectures can also be employed as the processing unit 1104.

The system bus 1108 can be any of several types of bus structure that can further interconnect to a memory bus (with or without a memory controller), a peripheral bus, and a local bus using any of a variety of commercially available bus architectures. The system memory 1106 includes ROM 1110 and RAM 1112. A basic input/output system (BIOS) can be stored in a non-volatile memory such as ROM, erasable programmable read only memory (EPROM), EEPROM, which BIOS contains the basic routines that help to transfer information between elements within the computer 1102, such as during startup. The RAM 1112 can also include a high-speed RAM such as static RAM for caching data.

The computer 1102 further includes an internal hard disk drive (HDD) 1114 (e.g., EIDE, SATA), one or more external storage devices 1116 (e.g., a magnetic floppy disk drive (FDD) 1116, a memory stick or flash drive reader, a memory card reader, etc.) and a drive 1120, e.g., such as a solid state drive, an optical disk drive, which can read or write from a disk 1122, such as a CD-ROM disc, a DVD, a BD, etc. Alternatively, where a solid state drive is involved, disk 1122 would not be included, unless separate. While the internal HDD 1114 is illustrated as located within the computer 1102, the internal HDD 1114 can also be configured for external use in a suitable chassis (not shown). Additionally, while not shown in environment 1100, a solid state drive (SSD) could be used in addition to, or in place of, an HDD 1114. The HDD 1114, external storage device(s) 1116 and drive 1120 can be connected to the system bus 1108 by an HDD interface 1124, an external storage interface 1126 and a drive interface 1128, respectively. The interface 1124 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1102, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1112, including an operating system 1130, one or more application programs 1132, other program modules 1134 and program data 1136. All or portions of the operating system, applications, modules, and/or data can also be cached in the RAM 1112. The systems and methods described herein can be implemented utilizing various commercially available operating systems or combinations of operating systems.

Computer 1102 can optionally comprise emulation technologies. For example, a hypervisor (not shown) or other intermediary can emulate a hardware environment for operating system 1130, and the emulated hardware can optionally be different from the hardware illustrated in FIG. 11. In such an embodiment, operating system 1130 can comprise one virtual machine (VM) of multiple VMs hosted at computer 1102. Furthermore, operating system 1130 can provide runtime environments, such as the Java runtime environment or the .NET framework, for applications 1132. Runtime environments are consistent execution environments that allow applications 1132 to run on any operating system that includes the runtime environment. Similarly, operating system 1130 can support containers, and applications 1132 can be in the form of containers, which are lightweight, standalone, executable packages of software that include, e.g., code, runtime, system tools, system libraries and settings for an application.

Further, computer 1102 can be enable with a security module, such as a trusted processing module (TPM). For instance with a TPM, boot components hash next in time boot components, and wait for a match of results to secured values, before loading a next boot component. This process can take place at any layer in the code execution stack of computer 1102, e.g., applied at the application execution level or at the operating system (OS) kernel level, thereby enabling security at any level of code execution.

A user can enter commands and information into the computer 1102 through one or more wired/wireless input devices, e.g., a keyboard 1138, a touch screen 1140, and a pointing device, such as a mouse 1142. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1104 through an input device interface 1144 that can be coupled to the system bus 1108, but can be connected by other interfaces, such as a parallel port, an IEEE 1394 serial port, a game port, a USB port, an IR interface, a BLUETOOTH® interface, etc.

A monitor 1146 or other type of display device can be also connected to the system bus 1108 via an interface, such as a video adapter 1148. In addition to the monitor 1146, a computer typically includes other peripheral output devices (not shown), such as speakers, printers, etc.

The computer 1102 can operate in a networked environment using logical connections via wired and/or wireless communications to one or more remote computers, such as a remote computer(s) 1150. The remote computer(s) 1150 can be a workstation, a server computer, a router, a personal computer, portable computer, microprocessor-based entertainment appliance, a peer device or other common network node, and typically includes many or all of the elements described relative to the computer 1102, although, for purposes of brevity, only a memory/storage device 1152 is illustrated. The logical connections depicted include wired/wireless connectivity to a local area network (LAN) 1154 and/or larger networks, e.g., a wide area network (WAN) 1156. Such LAN and WAN networking environments are commonplace in offices and companies, and facilitate enterprise-wide computer networks, such as intranets, all of which can connect to a global communications network, e.g., the Internet.

When used in a LAN networking environment, the computer 1102 can be connected to the local network 1154 through a wired and/or wireless communication network interface or adapter 1158. The adapter 1158 can facilitate wired or wireless communication to the LAN 1154, which can also include a wireless access point (AP) disposed thereon for communicating with the adapter 1158 in a wireless mode.

When used in a WAN networking environment, the computer 1102 can include a modem 1160 or can be connected to a communications server on the WAN 1156 via other means for establishing communications over the WAN 1156, such as by way of the Internet. The modem 1160, which can be internal or external and a wired or wireless device, can be connected to the system bus 1108 via the input device interface 1144. In a networked environment, program modules depicted relative to the computer 1102 or portions thereof, can be stored in the remote memory/storage device 1152. It will be appreciated that the network connections shown are example and other means of establishing a communications link between the computers can be used.

When used in either a LAN or WAN networking environment, the computer 1102 can access cloud storage systems or other network-based storage systems in addition to, or in place of, external storage devices 1116 as described above, such as but not limited to a network virtual machine providing one or more aspects of storage or processing of information. Generally, a connection between the computer 1102 and a cloud storage system can be established over a LAN 1154 or WAN 1156 e.g., by the adapter 1158 or modem 1160, respectively. Upon connecting the computer 1102 to an associated cloud storage system, the external storage interface 1126 can, with the aid of the adapter 1158 and/or modem 1160, manage storage provided by the cloud storage system as it would other types of external storage. For instance, the external storage interface 1126 can be configured to provide access to cloud storage sources as if those sources were physically connected to the computer 1102.

The computer 1102 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 12:
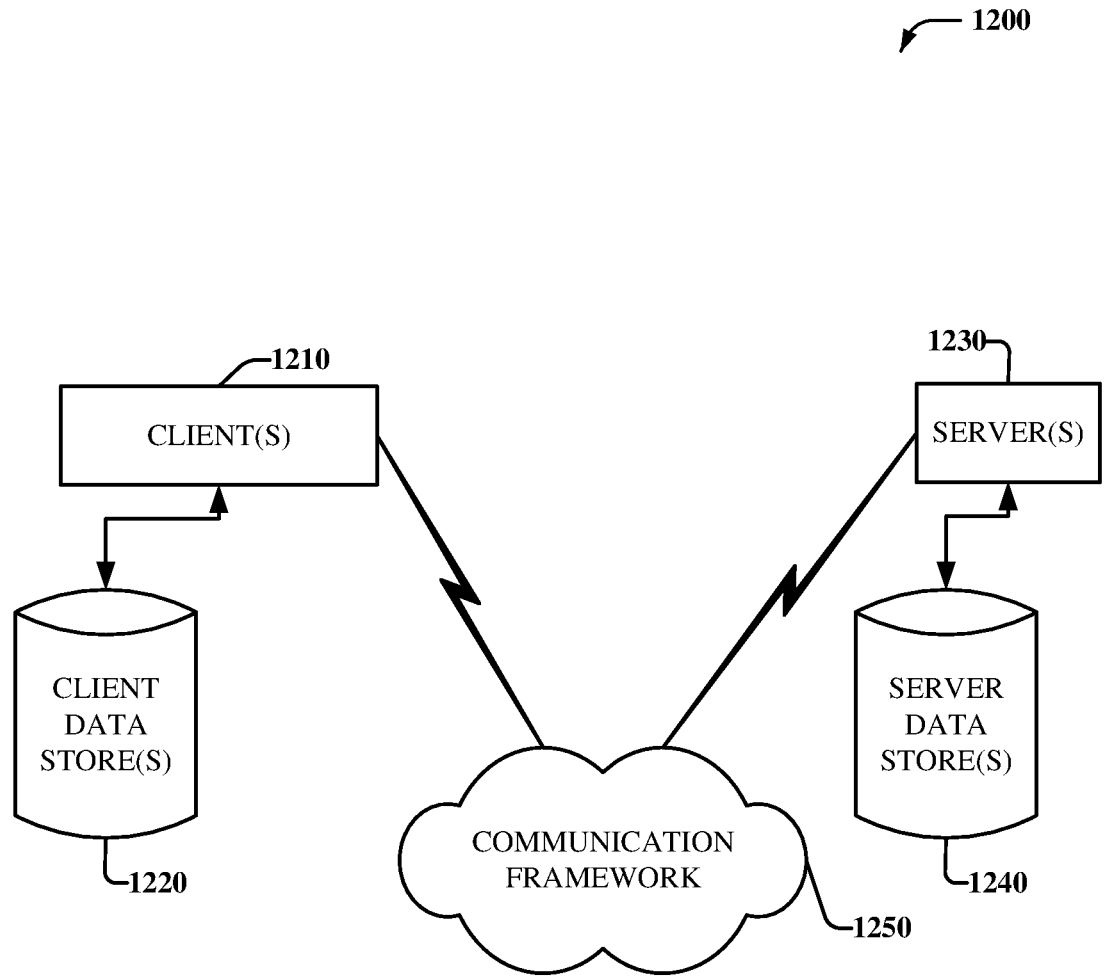
FIG. 12 illustrates an example networking environment operable to execute various implementations described herein.

FIG. 12 is a schematic block diagram of a sample computing environment 1200 with which the disclosed subject matter can interact. The sample computing environment 1200 includes one or more client(s) 1210. The client(s) 1210 can be hardware and/or software (e.g., threads, processes, computing devices). The sample computing environment 1200 also includes one or more server(s) 1230. The server(s) 1230 can also be hardware and/or software (e.g., threads, processes, computing devices). The servers 1230 can house threads to perform transformations by employing one or more embodiments as described herein, for example. One possible communication between a client 1210 and a server 1230 can be in the form of a data packet adapted to be transmitted between two or more computer processes. The sample computing environment 1200 includes a communication framework 1250 that can be employed to facilitate communications between the client(s) 1210 and the server(s) 1230. The client(s) 1210 are operably connected to one or more client data store(s) 1220 that can be employed to store information local to the client(s) 1210. Similarly, the server(s) 1230 are operably connected to one or more server data store(s) 1240 that can be employed to store information local to the servers 1230.

Various embodiments described herein may be a system, a method, an apparatus and/or a computer program product at any possible technical detail level of integration. The computer program product can include a computer readable storage medium (or media) having computer readable program instructions thereon for causing a processor to carry out aspects of various embodiments described herein. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various embodiments described herein can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of various embodiments described herein.

Aspects of various embodiments are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments described herein. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a processor that executes computer-executable components stored in a computer-readable memory, the computer-executable components comprising:
   a receiver component that accesses a first gantry angle of a medical scanner;
   a displacement component that determines a first displacement of a focal-spot of the medical scanner based on the first gantry angle, by referencing a mapping that correlates gantry angles to focal-spot displacements; and
   an execution component that compensates, via one or more focal-spot position adjusters of the medical scanner, for the first displacement.

2. The system of claim 1, wherein the receiver component further accesses a first voltage level of the medical scanner, wherein the mapping further correlates voltage levels to focal-spot displacements, and wherein the displacement component determines the first displacement of the focal-spot of the medical scanner based on the first voltage level.

3. The system of claim 1, further comprising:
   a calibration component that generates the mapping by:
   sweeping the medical scanner through a plurality of gantry angles; and
   measuring, at each of the plurality of gantry angles, how far and in what direction the focal-spot of the medical scanner has drifted from a predetermined position.

4. The system of claim 1, wherein the one or more focal-spot position adjusters cause the focal-spot to move in an opposite direction as the first displacement, and wherein the one or more focal-spot position adjusters cause the focal-spot to move by a distance that is equal to a magnitude of the first displacement.

5. The system of claim 1, wherein the one or more focal-spot position adjusters of the medical scanner are magnetic dipoles or electrostatic deflection electrodes.

6. The system of claim 1, wherein the medical scanner is a computed tomography scanner or a tomosynthesis mammography scanner.

7. The system of claim 1, wherein the receiver component accesses a second gantry angle of the medical scanner after the execution component compensates for the first displacement, wherein the displacement component determines a second displacement of the focal-spot of the medical scanner based on the second gantry angle, by referencing the mapping that correlates gantry angles to focal-spot displacements, and wherein the execution component compensates for the second displacement via the one or more focal-spot position adjusters of the medical scanner.

8. A computer-implemented method, comprising:
   accessing, by a device operatively coupled to a processor, a first gantry angle of a medical scanner;
   determining, by the device, a first displacement of a focal-spot of the medical scanner based on the first gantry angle, by referencing a mapping that correlates gantry angles to focal-spot displacements; and
   compensating, by the device and via one or more focal-spot position adjusters of the medical scanner, for the first displacement.

9. The computer-implemented method of claim 8, further comprising:
   accessing, by the device, a first voltage level of the medical scanner, wherein the mapping further correlates voltage levels to focal-spot displacements; and
   determining, by the device, the first displacement of the focal-spot of the medical scanner based on the first voltage level.

10. The computer-implemented method of claim 8, further comprising:
    generating, by the device, the mapping by:
    sweeping, by the device, the medical scanner through a plurality of gantry angles; and
    measuring, by the device and at each of the plurality of gantry angles, how far and in what direction the focal-spot of the medical scanner has drifted from a predetermined position.

11. The computer-implemented method of claim 8, wherein the one or more magnetic focal-spot position adjusters cause the focal-spot to move in an opposite direction as the first displacement, and wherein the one or more focal-spot position adjusters cause the focal-spot to move by a distance that is equal to a magnitude of the first displacement.

12. The computer-implemented method of claim 8, wherein the one or more focal-spot position adjusters of the medical scanner are magnetic dipoles or electrostatic deflection electrodes.

13. The computer-implemented method of claim 8, wherein the medical scanner is a computed tomography scanner or a tomosynthesis mammography scanner.

14. The computer-implemented method of claim 8, further comprising:
    accessing, by the device, a second gantry angle of the medical scanner after the compensating for the first displacement;
    determining, by the device, a second displacement of the focal-spot of the medical scanner based on the second gantry angle, by referencing the mapping that correlates gantry angles to focal-spot displacements; and
    compensating, by the device and via the one or more focal-spot position adjusters of the medical scanner, for the second displacement.

15. A computer program product for facilitating correction of intra-scan focal-spot displacement, the computer program product comprising a computer-readable memory having program instructions embodied therewith, the program instructions executable by a processor to cause the processor to:

access a first gantry angle of a medical scanner;

determine a first displacement of a focal-spot of the medical scanner based on the first gantry angle, by referencing a mapping that correlates gantry angles to focal-spot displacements; and compensate, by one or more focal-spot position adjusters of the medical scanner, for the first displacement.

16. The computer program product of claim 15, wherein the program instructions are further executable to cause the processor to:

access a first voltage level of the medical scanner, wherein the mapping further correlates voltage levels to focal-spot displacements; and determine the first displacement of the focal-spot of the medical scanner based on the first voltage level.

17. The computer program product of claim 15, wherein the program instructions are further executable to cause the processor to:

generate the mapping by:

sweeping the medical scanner through a plurality of gantry angles; and measuring, at each of the plurality of gantry angles, how far and in what direction the focal-spot of the medical scanner has drifted from a predetermined position.

18. The computer program product of claim 15, wherein the one or more focal-spot position adjusters cause the focal-spot to move in an opposite direction as the first displacement, and wherein the one or more focal-spot position adjusters cause the focal-spot to move by a distance that is equal to a magnitude of the first displacement.

19. The computer program product of claim 15, wherein the one or more focal-spot position adjusters of the medical scanner are magnetic dipoles or electrostatic deflection electrodes.

20. The computer program product of claim 15, wherein the medical scanner is a computed tomography scanner or a tomosynthesis mammography scanner.

\* \* \* \* \*